(12) United States Patent
Mou et al.

(10) Patent No.: US 11,169,069 B2
(45) Date of Patent: Nov. 9, 2021

(54) PARTICLE DETECTING MODULE

(71) Applicant: Microjet Technology Co., Ltd., Hsinchu (TW)

(72) Inventors: Hao-Jan Mou, Hsinchu (TW); Ching-Sung Lin, Hsinchu (TW); Chin-Chuan Wu, Hsinchu (TW); Chih-Kai Chen, Hsinchu (TW); Yung-Lung Han, Hsinchu (TW); Chi-Feng Huang, Hsinchu (TW); Chang-Yen Tsai, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 0 days.

(21) Appl. No.: 17/015,582

(22) Filed: Sep. 9, 2020

(65) Prior Publication Data

US 2021/0096052 A1 Apr. 1, 2021

(30) Foreign Application Priority Data

Sep. 27, 2019 (TW) .................................. 108135357
Nov. 7, 2019 (TW) .................................. 108140534

(51) Int. Cl.
   *G01N 15/02* (2006.01)

(52) U.S. Cl.
   CPC ................. *G01N 15/0211* (2013.01)

(58) Field of Classification Search
   CPC .... G01N 15/02; G01N 15/0205; G01N 15/06; G01N 15/10; G01N 15/1012; G01N 15/14; G01N 15/1425; G01N 15/1429; G01N 15/1431; G01N 15/1434; G01N 15/1436; G01N 15/1456; G01N 15/1459; G01N 15/147; G01N 15/1484
   USPC .......................................................... 356/336
   See application file for complete search history.

(56) References Cited

U.S. PATENT DOCUMENTS

| 10,935,478 | B2 * | 3/2021 | Mou ....................... G01N 15/02 |
| 2014/0377850 | A1 | 12/2014 | Handique et al. |
| 2020/0292437 | A1 * | 9/2020 | Mou ....................... G01N 15/06 |
| 2020/0292438 | A1 * | 9/2020 | Mou ................... G01N 15/0211 |
| 2021/0099105 | A1 * | 4/2021 | Mou ................... G01N 33/0009 |
| 2021/0109004 | A1 * | 4/2021 | Mou ................... G01N 33/0009 |
| 2021/0188050 | A1 * | 6/2021 | Mou ................... B01D 46/0028 |
| 2021/0205751 | A1 * | 7/2021 | Mou ....................... F24F 11/30 |
| 2021/0208049 | A1 * | 7/2021 | Mou ................... G01N 15/0205 |
| 2021/0208120 | A1 * | 7/2021 | Mou ................... G01N 33/0027 |

* cited by examiner

*Primary Examiner* — Roy M Punnoose
(74) *Attorney, Agent, or Firm* — Birch, Stewart, Kolasch & Birch, LLP

(57) ABSTRACT

A particle detecting module is provided. The particle detecting module includes a base, a piezoelectric actuator, a driving circuit board, a laser component, a particulate sensor and an outer cover. A gas-guiding-component loading regain and a laser loading region are separated by the base. By the design of the gas flowing path, the driving circuit board covering the bottom surface of the base, and the outer cover covering the surfaces of the base, an inlet path is defined by the gas inlet groove of the base, and an outlet path is defined by a gas outlet groove of the base. Consequently, the thickness of the particle detecting module is drastically reduced.

15 Claims, 25 Drawing Sheets

PARTICLE DETECTING MODULE

FIELD OF THE INVENTION

The present disclosure relates to a particle detecting module, and more particularly to an extremely thin particle detecting module.

BACKGROUND OF THE INVENTION

Suspended particles are solid particles or droplets contained in the air. Since the sizes of the suspended particles are really small, the suspended particles may enter the lungs of human body through the nasal hair in the nasal cavity easily, thus causing inflammation in the lungs, asthma or cardiovascular disease. If other pollutants are attached to the suspended particles, it will further increase the harm to the respiratory system. In recent years, the problem of air pollution is getting worse. In particular, the concentration of particle matters (e.g., PM2.5) is often too high. Therefore, the monitoring to the concentration of the gas suspended particles is taken seriously. However, the gas flows unstably due to variable wind direction and air volume, and the general gas-quality monitoring station is located in a fixed place. Under this circumstance, it is impossible for people to check the concentration of suspended particles in current environment. Thus, a miniature and portable particle detecting module is needed for allowing the user to check the concentration of surrounding suspended particles anytime and anywhere.

Please refer to FIG. 1, which shows a particle detecting module disclosed in Taiwan Patent Application No. 107130404. In the particle detecting module 1A according to the prior art, it is difficult to reduce the volume of the housing 11A due to the limitations of the size of the gas-guiding component 12A and the internal gas flow channel. A gas-guiding path is shown by the arrows in FIG. 1. After gas is introduced from the inlet in the upper level and then flows downwardly to the lower level, a detection is performed. Then, the detected gas is transported through the micro pump, flows back to the upper level and is discharged through the outlet finally. In the structure of the conventional gas-guiding channel, the gas-guiding path is designed in multiple layers, which is complex and thicker. It is difficult to reduce the entire thickness of the particle detecting module, and it is more difficult to implement the conventional particle detecting module on a miniaturized mobile device or other portable electronic devices. Therefore, how to make the particle detecting module thinner and lighter is a problem that urgently needs to be solved.

SUMMARY OF THE INVENTION

An object of the present disclosure provides a particle detecting module. With a driving circuit board attached to a second surface of a base, and a first surface of the base covered with an outer cover, an inlet path is defined in a gas-inlet groove, and an outlet path is defined in the gas-outlet groove. In addition, the laser component is arranged on the driving circuit board, the driving circuit board directly covers the base, and the position of the piezoelectric actuator is separated from the position of the laser component. It benefits to reduce the thickness of the particle detecting module greatly.

In accordance with an aspect of the present disclosure, a particle detecting module is provided. The particle detecting module includes a base, a piezoelectric actuator, a driving circuit board, a laser component, a particulate sensor and an outer cover. The base includes a first substrate, a second surface, a laser loading region, a gas-inlet groove, a gas-guiding component loading region and a gas-outlet groove. The second surface is opposite to the first surface. The laser loading region is hollowed out from the first surface to the second surface. The gas-inlet groove is concavely formed from the second surface and disposed adjacent to the laser loading region. The gas-inlet groove includes a gas-inlet and two lateral walls, the gas-inlet is in communication with an environment outside the base, and the two lateral walls are extended towards a transparent window is opened on the lateral wall and is in communication to the laser loading region. The gas-guiding-component loading region is concavely formed from the second surface and in fluid communication with the gas-inlet groove. A ventilation hole penetrates through a bottom surface of the gas-guiding-component loading region. The gas-outlet groove is concavely formed from the first surface, spatially corresponds to the bottom surface of the gas-guiding-component loading region, and is hollowed out from the first surface to the second surface in a region where the first surface is not aligned with the gas-guiding-component loading region. The gas-outlet groove is in communication with the ventilation hole, and a gas-outlet is disposed in the gas-outlet groove and in communication with the environment outside the base. The piezoelectric actuator is accommodated in the gas-guiding-component loading region. The driving circuit board covers and is attached to the second surface of the base. The laser component is positioned and disposed on the driving circuit board, electrically connected to the driving circuit board, and accommodated in the laser loading region. A light beam path emitted from the laser component passes through the transparent window and extends in a direction perpendicular to the gas-inlet groove, thereby forming an orthogonal direction with the gas-inlet groove. The particulate sensor is positioned and disposed on the driving circuit board, electrically connected to the driving circuit board, and disposed at an orthogonal position where the gas-inlet groove intersects the light beam path of the laser component in the orthogonal direction, so that suspended particles passing through the gas-inlet groove and irradiated by a projecting light beam emitted from the laser component are detected. The outer cover covers the first surface of the base and includes a side plate. The side plate has an inlet opening spatially corresponding to the gas-inlet and an outlet opening spatially corresponding to the gas-outlet, respectively. The first surface of the base is covered with the outer cover, and the second surface of the base is covered with the driving circuit board, so that an inlet path is collaboratively defined by the gas-inlet groove and the driving circuit board, and an outlet path is collaboratively defined by the gas-outlet groove, the outer cover and the driving circuit board. The gas is inhaled from the environment outside the base by the piezoelectric actuator, transported into the inlet path through the inlet opening, and passes through the particulate sensor to detect a concentration of the suspended particles contained in the gas, and the gas transported through the piezoelectric actuator is transported out of the outlet path through the ventilation hole and then discharged through the outlet opening.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1:
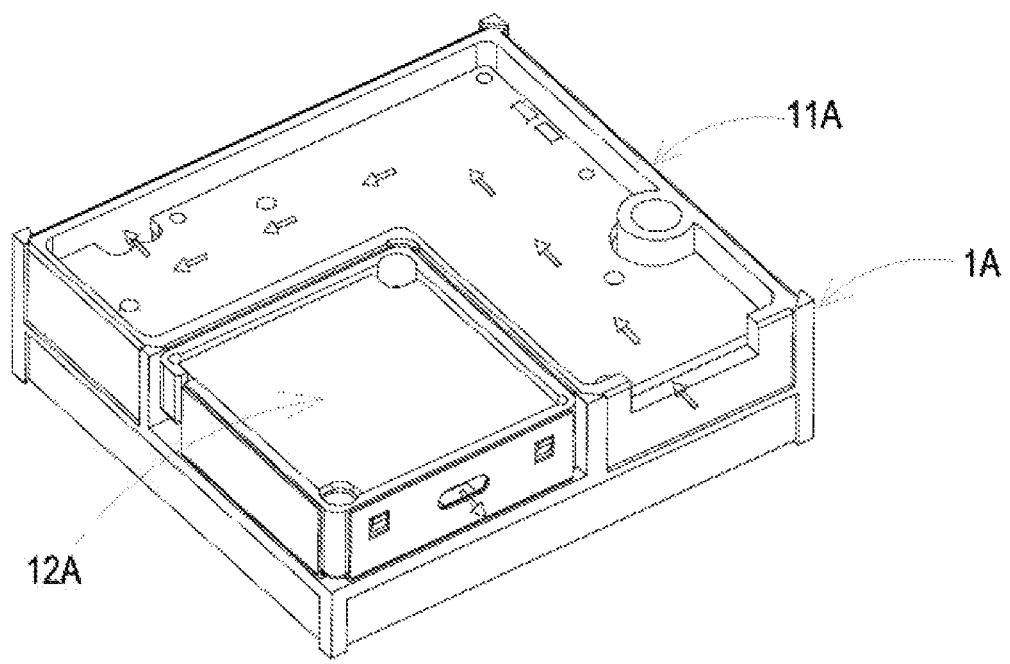
FIG. 1 shows a particle detecting module according to the prior art.
Figure 2A:
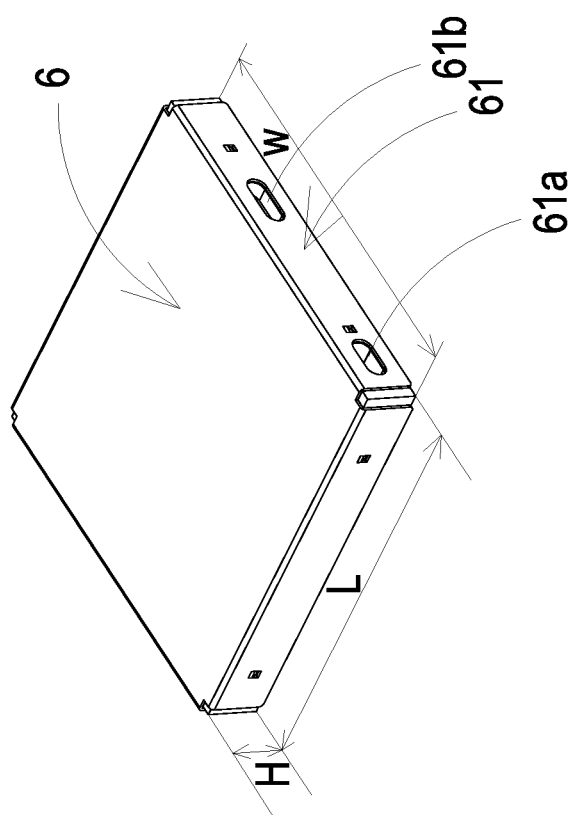
FIG. 2A is a schematic exterior view illustrating a particle detecting module according to an embodiment of the present disclosure.
Figure 2B:
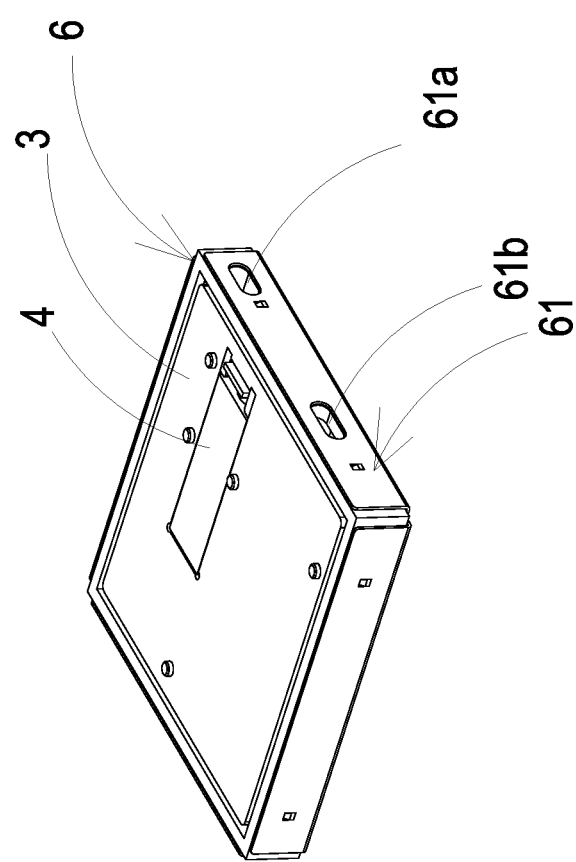
FIG. 2B is a schematic exterior view illustrating the particle detecting module according to the embodiment of the present disclosure and taken from another perspective angle.
Figure 2C:
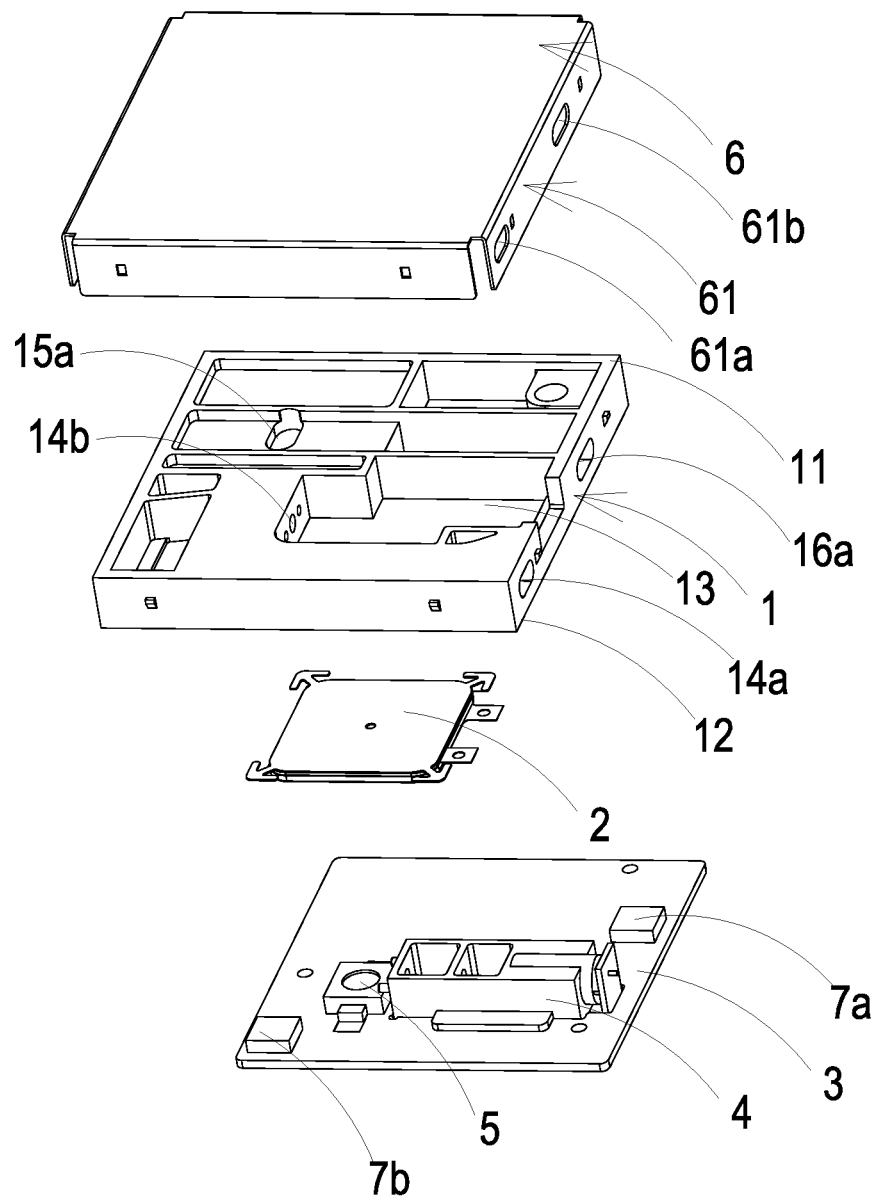
FIG. 2C is a schematic exploded view illustrating the particle detecting module of the present disclosure.

Please refer to FIGS. 2A to 2C. The present disclosure provides a particle detecting module 100 including a base 1, a piezoelectric actuator 2, a driving circuit board 3, a laser component 4, a particulate sensor 5 and an outer cover 6. Moreover, the base 1, the piezoelectric actuator 2, the driving circuit board 3, the laser component 4, the particulate sensor 5 and the outer cover 6 are produced by tiny materials to form a modular structure, and the modular structure has a length, a width and a thickness. Each of the length, the width and the thickness of the modular structure is ranging from 1 mm to 999 mm, 1 μm to 999 μm or 1 nm to 999 nm, but not limited thereto. In the embodiment, the modular structure is assembled by the base 1, the piezoelectric actuator 2, the driving circuit board 3, the laser component 4, the particulate sensor 5 and the outer cover 6, the length of the modular structure is ranging from 1 μm to 999 μm, the width of the modular structure is ranging from 1 μm to 999 μm, and the thickness of the modular structure is ranging from 1 μm to 999 μm, so as to form the volume of the modular structure. In other embodiment, the length of the modular structure is ranging from 1 nm to 999 nm, the width of the modular structure is ranging from 1 nm to 999 nm, and the thickness of the modular structure is ranging from 1 nm to 999 nm, so as to form the volume of the modular structure. The present disclosure is not limited thereto. In the embodiment, the driving circuit board 3 covers and is attached to the second surface 12 of the base 1, and the laser component 4 is positioned and disposed on the driving circuit board 3, and is electrically connected to the driving circuit board 3. The particulate sensor 5 is positioned and disposed on the driving circuit board 3, and is electrically connected to the driving circuit board 3. The outer cover 6 covers the base 1 and is attached to the first surface 11 of the base 1. Moreover, the outer cover 6 includes a side plate 61. The side plate 61 includes an inlet opening 61a and an outlet opening 61b.

Figure 3A:
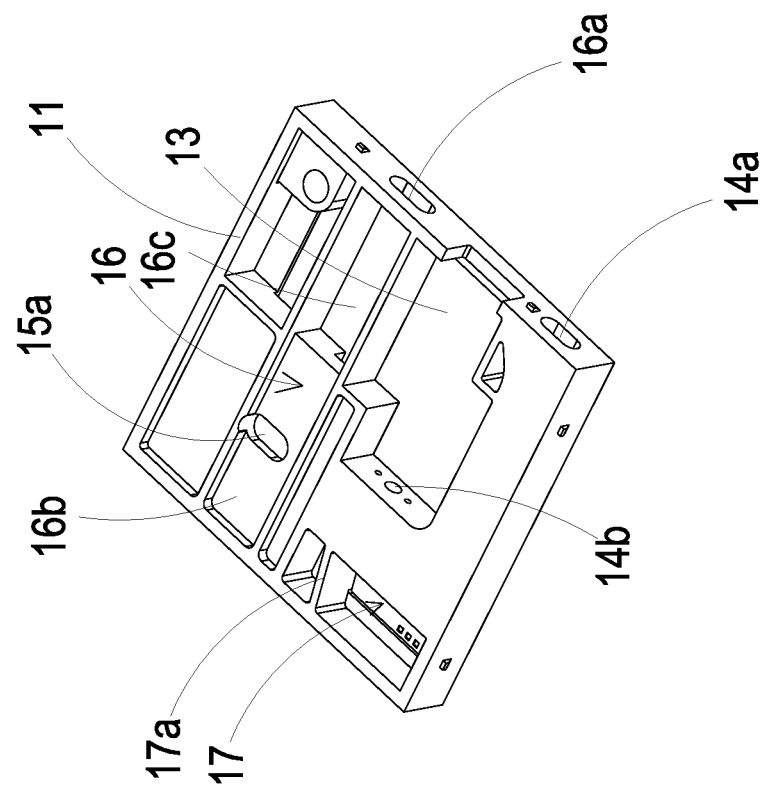
FIG. 3A is a schematic perspective view illustrating a base of the particle detecting module of the present disclosure.
Figure 3B:
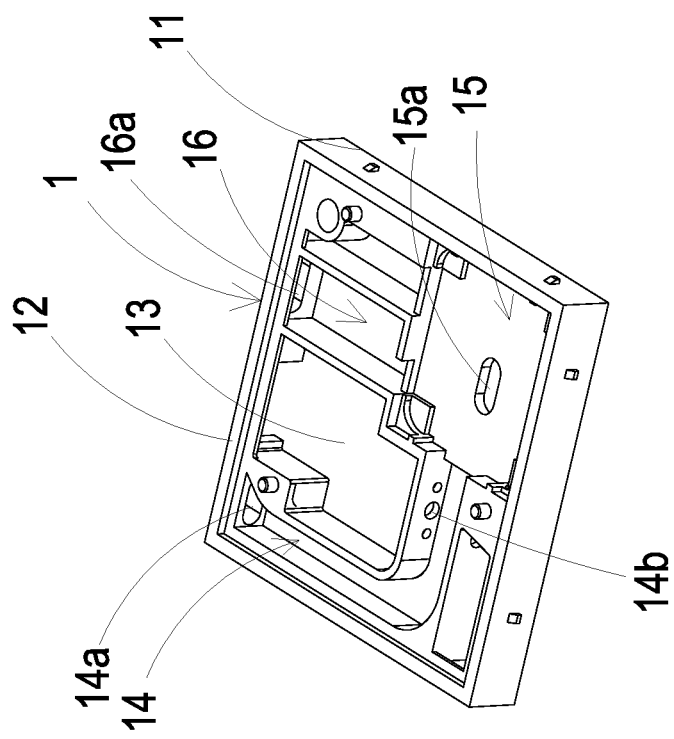
FIG. 3B is a schematic perspective view illustrating the base of the particle detecting module of the present disclosure and taken from another perspective angle.

Please refer to FIG. 3A and FIG. 3B. In the embodiment, the base 1 includes a first surface 11, a second surface 12, a laser loading region 13, a gas-inlet groove 14, a gas-guiding-component loading region 15 and a gas-outlet groove 16. The first surface 11 and the second surface 12 are two opposite surfaces. The laser loading region 13 is hollowed out from the first surface 11 to the second surface 12. The gas-inlet groove 14 is concavely formed from the second surface 12 and disposed adjacent to the laser loading region 13. The gas-inlet groove 14 includes a gas-inlet 14a and two lateral walls. The gas-inlet 14a is in communication with the an environment outside the base 1 and spatially corresponds to the inlet opening 61a of the outer cover 6. A transparent window 14b is opened on the lateral wall and is in communication to the laser loading region 13. In that, the first surface 11 of the base 1 is attached and covered by the outer cover 6, and the second surface 12 of the base 1 is attached and covered by the driving circuit board 3, so that an inlet path is collaboratively defined by the gas-inlet groove 14 and the driving circuit board 3.

In the embodiment, the gas-guiding-component loading region 15 is concavely formed from the second surface 12 and in communication with the gas-inlet groove 14. A ventilation hole 15a penetrates through a bottom surface of the gas-guiding-component loading region 15. The gas-outlet groove 16 includes a gas-outlet 16a, and the gas-outlet 16a spatially corresponds to the outlet opening 61b of the outer cover 6. The gas-outlet groove 16 includes a first section 16b and a second section 16c. The first section 16b is hollowed out from the first surface 11 to the second surface 12 in a vertical projection area of the gas-guiding-component loading region 15 spatially corresponds thereto. The second section 16c is hollowed out from the first surface 11 to the second surface 12 in a region where the first surface 11 is not aligned with the vertical projection area of the gas-guiding-component loading region 15 and extended therefrom. The first section 16b and the second section 16c are connected to form a stepped structure. Moreover, the first section 16b of the gas-outlet groove is in communication with the ventilation hole 15a of the gas-guiding-component loading region 15, and the second section 16c of the gas-outlet groove 16 is in communication with the gas-outlet 16a. In that, the first surface 11 of the base 1 is attached and covered by the outer cover 6, and the second surface 12 of the base 1 is attached and covered by the driving circuit board 3, so that an outlet path is collaboratively defined by the gas-outlet groove 16, the outlet cover 6 and the driving circuit board 3.

Figure 4:
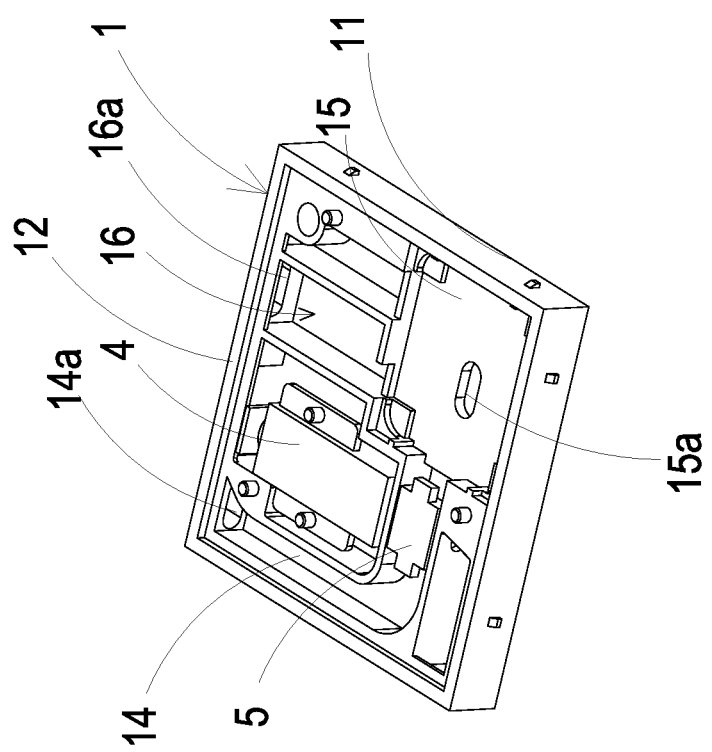
FIG. 4 is a schematic perspective view illustrating a laser component and a particulate sensor accommodated in the base of the present disclosure.

FIG. 4 is a schematic perspective view illustrating a laser component and a particulate sensor accommodated in the base of the present disclosure. In the embodiment, the laser component 4 and the particulate sensor 5 are disposed on the driving circuit board 3 and accommodated in the base 1. In order to describe the positions of the laser component 4 and the particulate sensor 5 in the base 1, the driving circuit board 3 is specifically omitted in FIG. 3 to explain clearly. Please refer to FIG. 4 and FIG. 2C. The laser component 4 is accommodated in the laser loading region 13 of the base 1, and the particulate sensor 5 is accommodated in the gas-inlet groove 14 of the base 1 and aligned to the laser component 4. In addition, the laser component 4 spatially corresponds to the transparent window 14b, a light beam emitted by the laser component 4 passes through the transparent window 14b and is irradiated into the gas-inlet groove 14. A light beam path emitted from the laser component 4 passes through the transparent window 14b and extends in a direction perpendicular to the gas-inlet groove, thereby forming an orthogonal direction with the gas-inlet groove 14.

In the embodiment, a projecting light beam emitted from the laser component 4 passes through the transparent window 14b and enters the gas-inlet groove 14, and suspended particles contained in the gas passing through the gas-inlet groove 14 is irradiated by the projecting light beam. When the suspended particles contained in the gas are irradiated to generate scattered light spots, the scattered light spots are received and calculated by the particulate sensor 5 for obtaining related information about the sizes and the concentration of the suspended particles contained in the gas. In the embodiment, the particulate sensor 5 is a PM2.5 sensor.

Figure 5A:
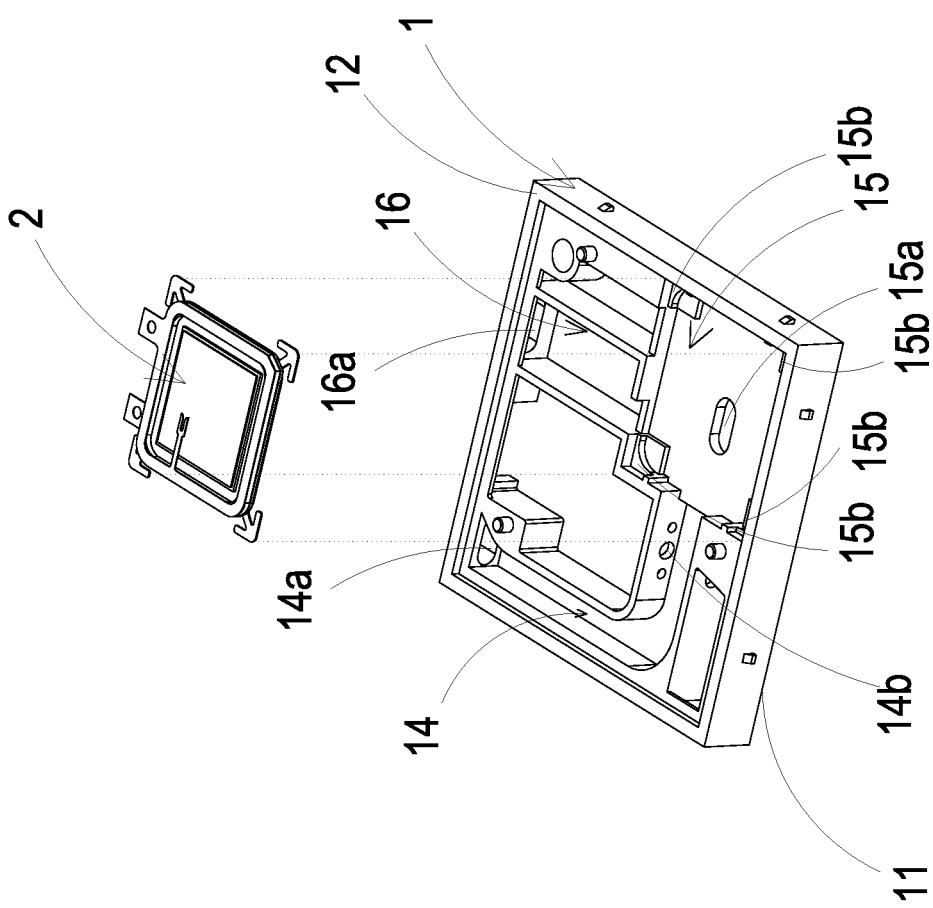
FIG. 5A is a schematic exploded view illustrating the combination of the piezoelectric actuator and the base.
Figure 5B:
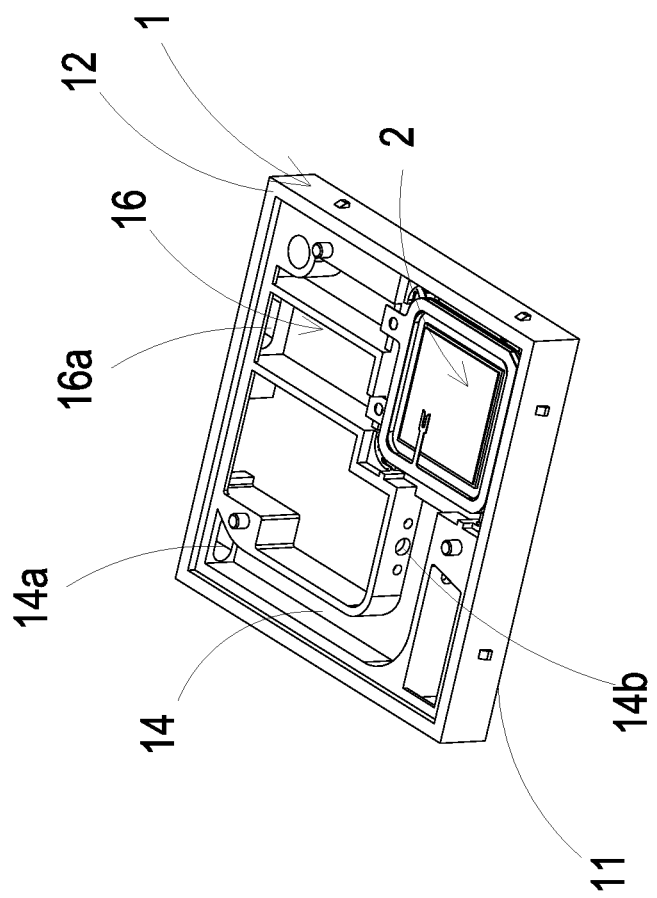
FIG. 5B is a schematic perspective view illustrating the combination of the piezoelectric actuator and the base.

Please refer to FIG. 5A and FIG. 5B. The piezoelectric actuator 2 is accommodated in the gas-guiding-component loading region of the base 1. Preferably but not exclusively, the gas-guiding-component loading region 15 is square and includes four positioning notches 15b disposed at four corners of the gas-guiding-component loading region 15, respectively. The piezoelectric actuator 2 is disposed in the gas-guiding-component loading region 15 through the four positioning notches 15b. In addition, the gas-guiding-component loading region 15 is in fluid communication with the gas-inlet groove 14. When the piezoelectric actuator 2 is enabled, the gas in the gas-inlet groove 14 is inhaled by the piezoelectric actuator 2, so that the gas flows into the piezoelectric actuator 2. Furthermore, the gas is transported into the gas-outlet groove 16 through the ventilation hole 15a of the gas-guiding-component loading region 15.

Figure 6A:
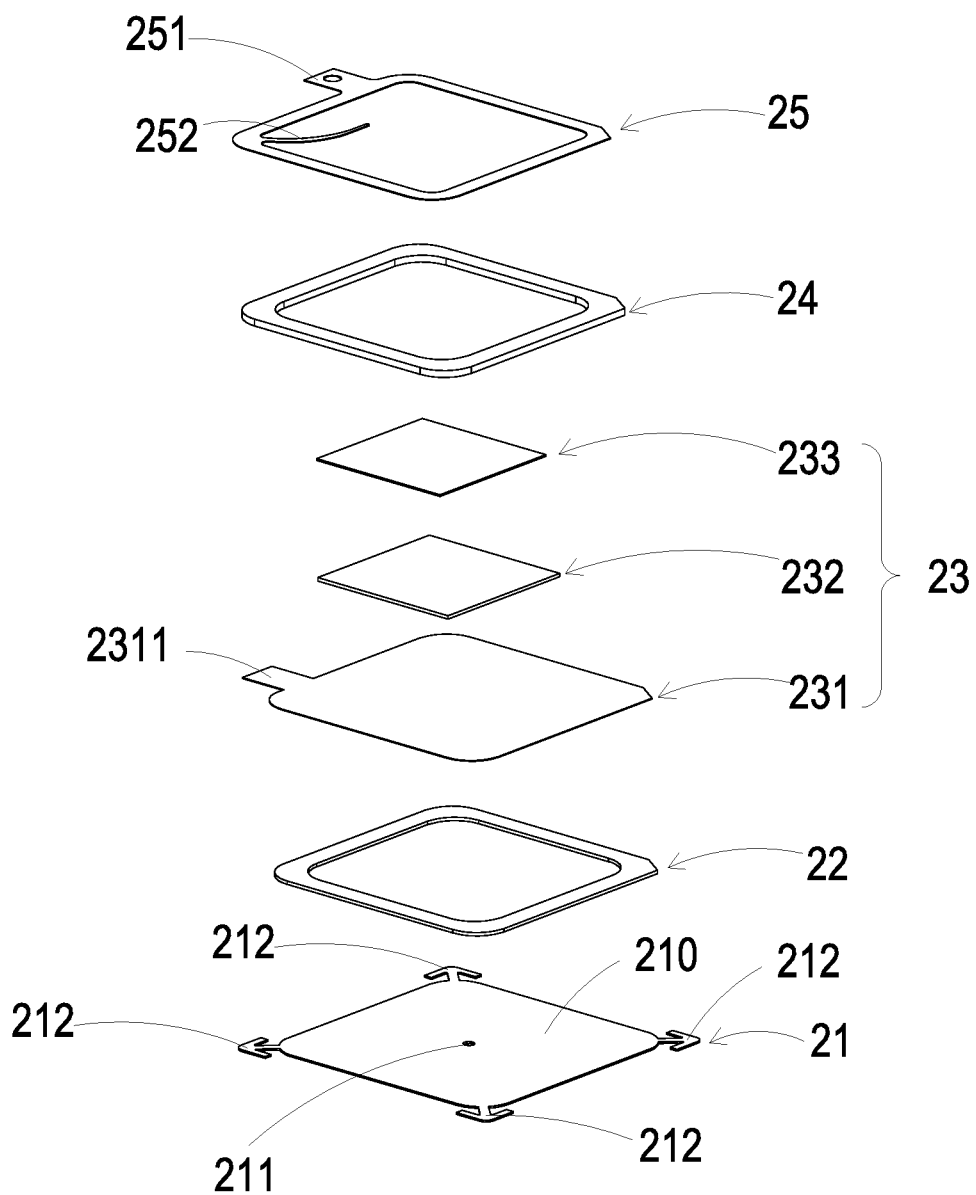
FIG. 6A is a schematic exploded view illustrating the piezoelectric actuator.
Figure 6B:
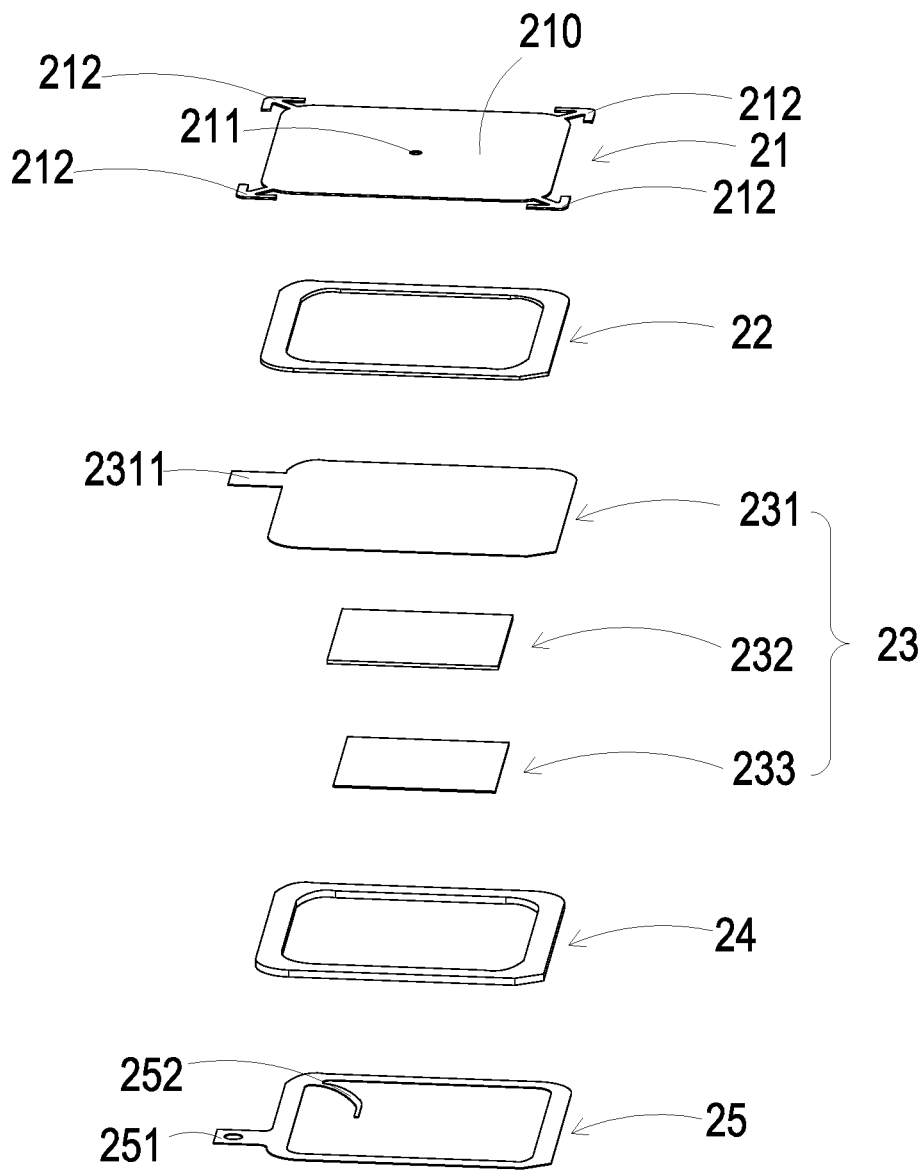
FIG. 6B is a schematic exploded view illustrating the piezoelectric actuator and taken from another perspective angle.

Please refer to FIGS. 6A and 6B. In the embodiment, the piezoelectric actuator 2 includes a gas-injection plate 21, a chamber frame 22, an actuator element 23, an insulation frame 24 and a conductive frame 25.

In the embodiment, the gas-injection plate 21 is made by a flexible material and includes a suspension plate 210, a hollow aperture 211 and a plurality of connecting elements 212. The suspension plate 210 is a sheet structure and permitted to undergo a bending deformation. Preferably but not exclusively, the shape and the size of the suspension plate 210 are corresponding to an inner edge of the gas-guiding-component loading region 15. The shape of the suspension plate 210 is one selected from the group consisting of a square, a circle, an ellipse, a triangle and a polygon. The hollow aperture 211 passes through a center of the suspension plate 210, so as to allow the gas to flow through. The connecting elements 212 are connected to and adjacent to the periphery of the suspension plate 2 for elastically supporting. In this embodiment, the gas-injection plate 21 includes four connecting elements 212. The number and profile of the connecting elements 212 are mainly corresponding to the positioning notches 15b of the gas-guiding-component loading region 15. Consequently, a fastening structure is established between each connecting element 212 and the corresponding positioning notch 15b, so that each connecting element 212 and the corresponding positioning notch 15b can be matched and fastened to each other. In that, the piezoelectric actuator 2 is disposed in the gas-guiding-component loading region 15.

The chamber frame 22 is carried and stacked on the gas-injection plate 21. In addition, the shape of the chamber frame 22 is corresponding to the gas-injection plate 21. The actuator element 23 is carried and stacked on the chamber frame 22. A resonance chamber 26 is collaboratively defined by the actuator element 23, the chamber frame 22 and the suspension plate 210 and formed among the actuator element 23, the chamber frame 22 and the suspension plate 210. The insulation frame 24 is carried and stacked on the actuator element 23 and the appearance of the insulation frame 24 is similar to that of the chamber frame 22. The conductive frame 25 is carried and stacked on the insulation frame 24, and the appearance of the conductive frame 25 is similar to that of the insulation frame 24. In addition, the conductive frame 25 includes a conducting pin 251 and a conducting electrode 252. The conducting pin 251 is extended outwardly from an outer edge of the conductive frame 25, and the conducting electrode 252 is extended inwardly from an inner edge of the conductive frame 25. Moreover, the actuator element 23 further includes a piezoelectric carrying plate 231, an adjusting resonance plate 232 and a piezoelectric plate 233. The piezoelectric carrying plate 231 is carried and stacked on the chamber frame 22. The adjusting resonance plate 232 is carried and stacked on the piezoelectric carrying plate 231. The piezoelectric plate 233 is carried and stacked on the adjusting resonance plate 232. The adjusting resonance plate 232 and the piezoelectric plate 233 are accommodated in the insulation frame 24. The conducting electrode 252 of the conductive frame 25 is electrically connected to the piezoelectric plate 233. In the embodiment, the piezoelectric carrying plate 231 and the adjusting resonance plate 232 are made by a conductive material. The piezoelectric carrying plate 231 includes a piezoelectric pin 2311. The piezoelectric pin 2311 and the conducting pin 251 are electrically connected to a driving circuit (not shown) of the driving circuit board 3, so as to receive a driving signal, such as a driving frequency and a driving voltage. In that, a loop is formed by the piezoelectric pin 2311, the piezoelectric carrying plate 231, the adjusting resonance plate 232, the piezoelectric plate 233, the conducting electrode 252, the conductive frame 25 and the conducting pin 251 for the driving signal. Moreover, the insulation frame 24 is insulated between the conductive frame 25 and the actuator element 23, so as to avoid the occurrence of a short circuit. Thereby, the driving signal is transmitted to the piezoelectric plate 233. After receiving the driving signal such as the driving frequency and the driving voltage, the piezoelectric plate 233 deforms due to the piezoelectric effect, and the piezoelectric carrying plate 231 and the adjusting resonance plate 232 are further driven to generate the bending deformation in the reciprocating manner.

As described above, the adjusting resonance plate 232 is located between the piezoelectric plate 233 and the piezoelectric carrying plate 231 and served as a buffer between the piezoelectric plate 233 and the piezoelectric carrying plate 231. Thereby, the vibration frequency of the piezoelectric carrying plate 231 is adjustable. Basically, the thickness of the adjusting resonance plate 232 is greater than the thickness of the piezoelectric carrying plate 231, and the thickness of the adjusting resonance plate 232 is adjustable, thereby adjusting the vibration frequency of the actuator element 23.

Figure 7A:
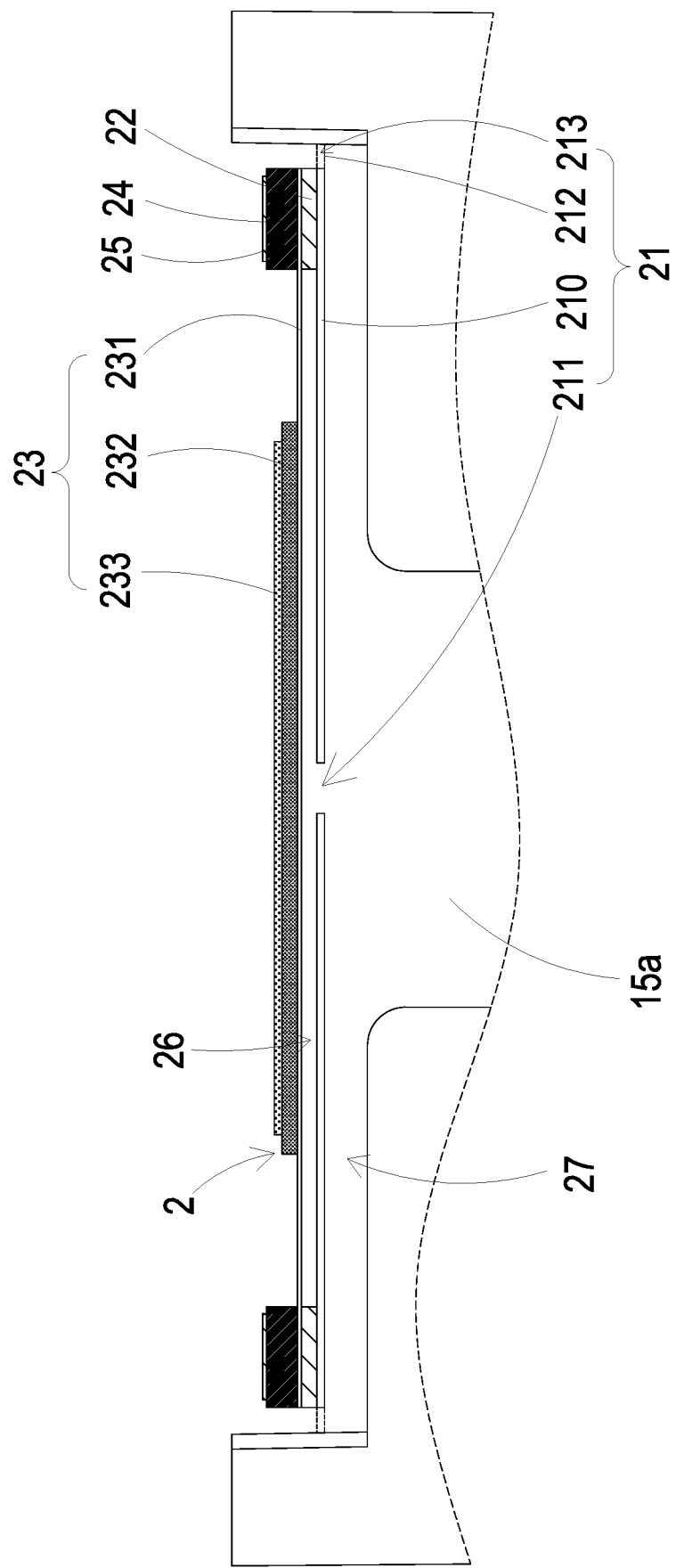
FIG. 7A is a schematic cross-sectional view illustrating the piezoelectric actuator accommodated in the gas-guiding-component loading region.

Please refer to FIGS. 6A, 6B and FIG. 7A. A plurality of vacant spaces 213 is defined by the plurality of connecting elements 212 between the suspension plate 210 and an inner edge of the gas-guiding-component loading region 15 in the piezoelectric actuator 2, and is provided for gas flowing.

Please refer to FIG. 7A. The gas-injection plate 21, the chamber frame 22, the actuator element 23, the insulation frame 24 and the conductive frame 25 are stacked and positioned in the gas-guiding-component loading region 15 sequentially, and a flowing chamber 27 is formed between the gas-injection plate 21 and the bottom surface of the gas-guiding-component loading region 15. The flowing chamber 27 is in fluid communication with the resonance chamber 26 among the actuator element 23, the chamber frame 22 and the suspension plate 210 through the hollow aperture 211 of the gas-injection plate 21. By controlling the vibration frequency of the gas in the resonance chamber 26 to be close to the vibration frequency of the suspension plate 210, the Helmholtz resonance effect is generated between the resonance chamber 26 and the suspension plate 210, and thereby the efficiency of gas transportation is improved.

Figure 7B:
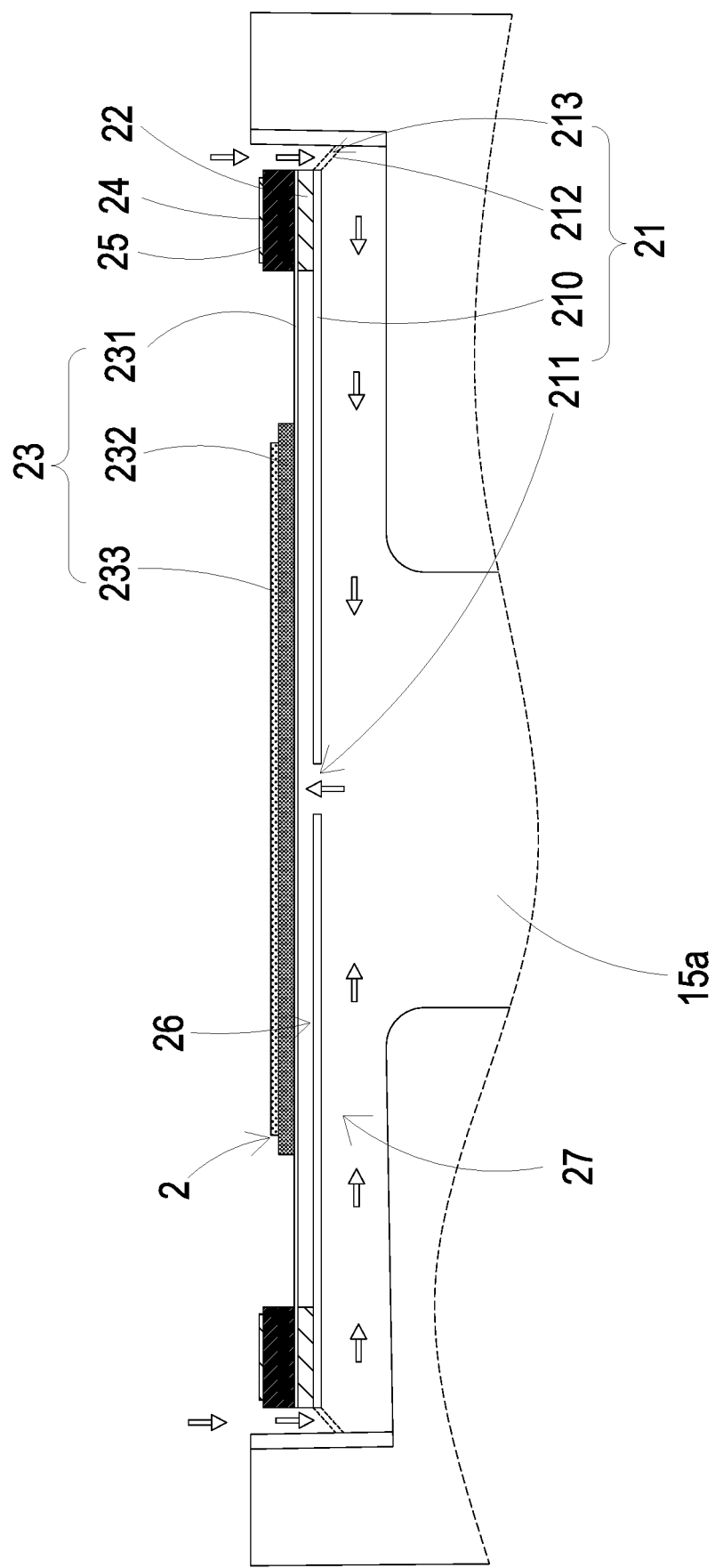
FIGS. 7B and 7C schematically illustrate the actions of the piezoelectric actuator of FIG. 7A.
Figure 7C:
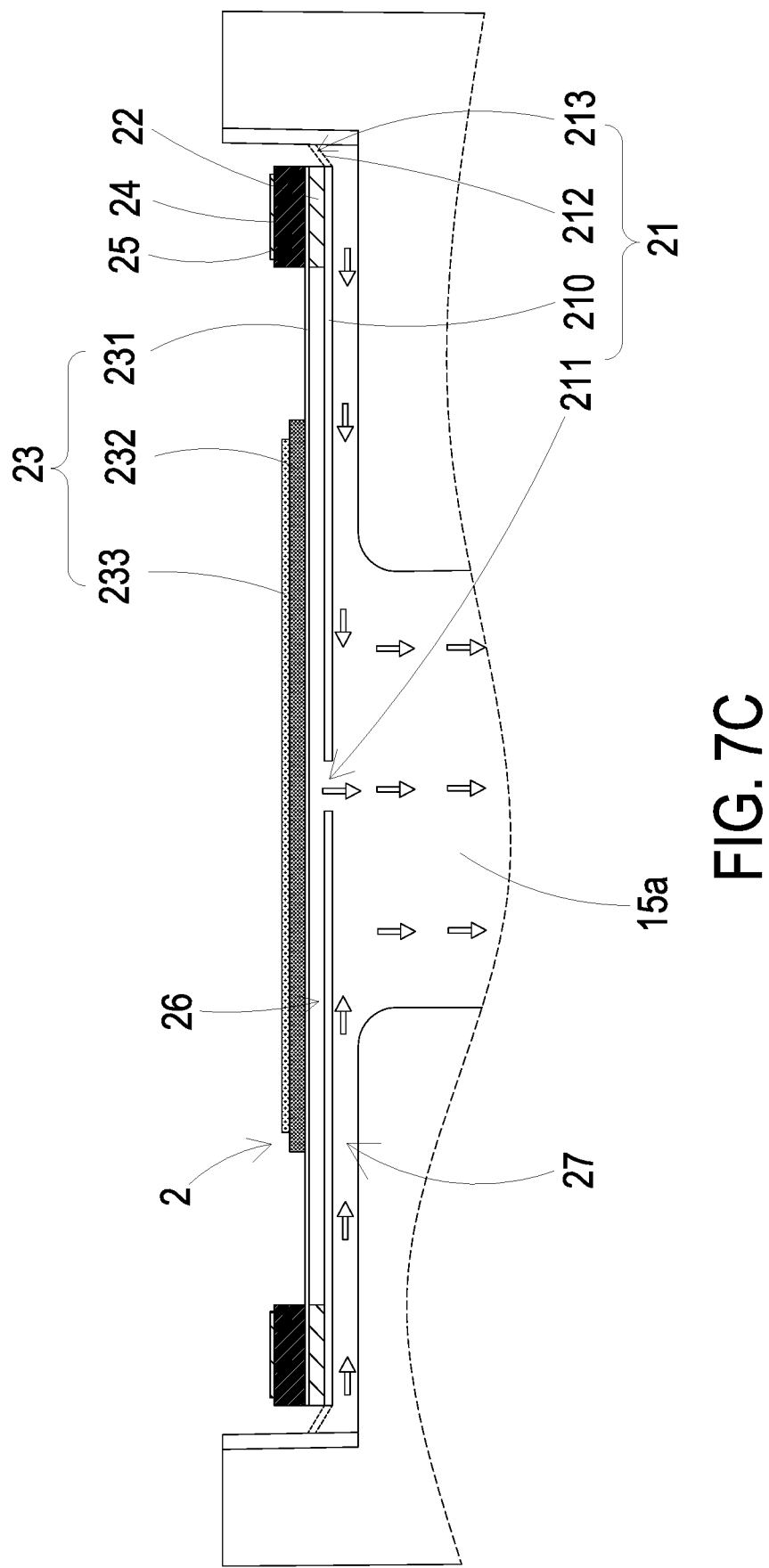

FIGS. 7B and 7C schematically illustrate the actions of the piezoelectric actuator of FIG. 7A. Please refer to FIG. 7B. When the piezoelectric plate 233 is moved away from the bottom surface of the gas-guiding-component loading region 15, the suspension plate 210 of the gas-injection plate 21 is moved away from the bottom surface of the gas-guiding-component loading region 15. In that, the volume of the flowing chamber 27 is expanded rapidly, the internal pressure of the flowing chamber 27 is decreased to form a negative pressure, and the gas outside the piezoelectric actuator 2 is inhaled through the vacant space 213 and enters the resonance chamber 26 through the hollow aperture 211. Consequently, the pressure in the resonance chamber 26 is increased to generate a pressure gradient. Further as shown in FIG. 7C, when the suspension plate 210 of the gas-injection plate 21 is driven by the piezoelectric plate 233 to move towards the bottom surface of the gas-guiding-component loading region 15, the gas in the resonance chamber 26 is discharged out rapidly through the hollow aperture 211, and the gas in the flowing chamber 27 is compressed. In that, the converged gas close to an ideal gas state of the Benulli's law is quickly and massively ejected and introduced into the ventilation hole 15a of the gas-guiding-component loading region 15. By repeating the above actions shown in FIG. 7B and FIG. 7C, the piezoelectric plate 233 is driven to generate the bending deformation in a reciprocating manner. Moreover, according to the principle of inertia, since the gas pressure inside the resonance chamber 26 after exhausting is lower than the equilibrium gas pressure, the gas is introduced into the resonance chamber 26 again. Thus, the vibration frequency of the gas in the resonance chamber 26 is controlled to be close to the vibration frequency of the piezoelectric plate 233, so as to generate the Helmholtz resonance effect to achieve the gas transportation at high speed and in large quantities.

Figure 8A:
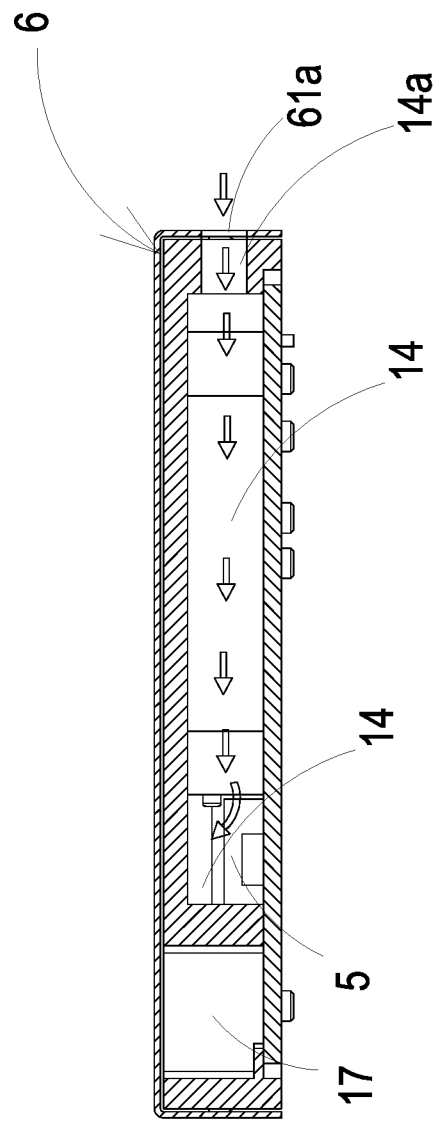
FIGS. 8A to 8C schematically illustrate gas flowing paths of the particle detecting module.
Figure 8B:
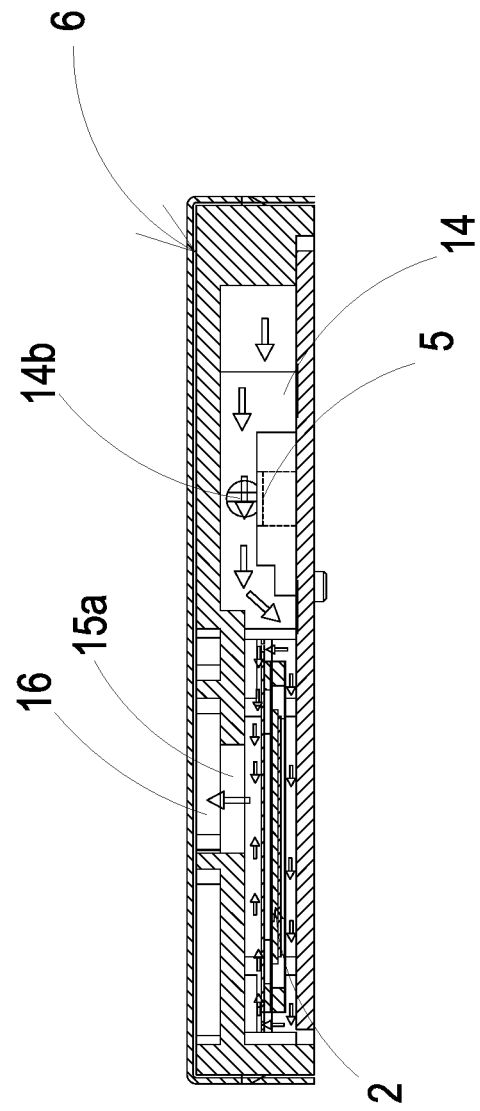
Figure 8C:
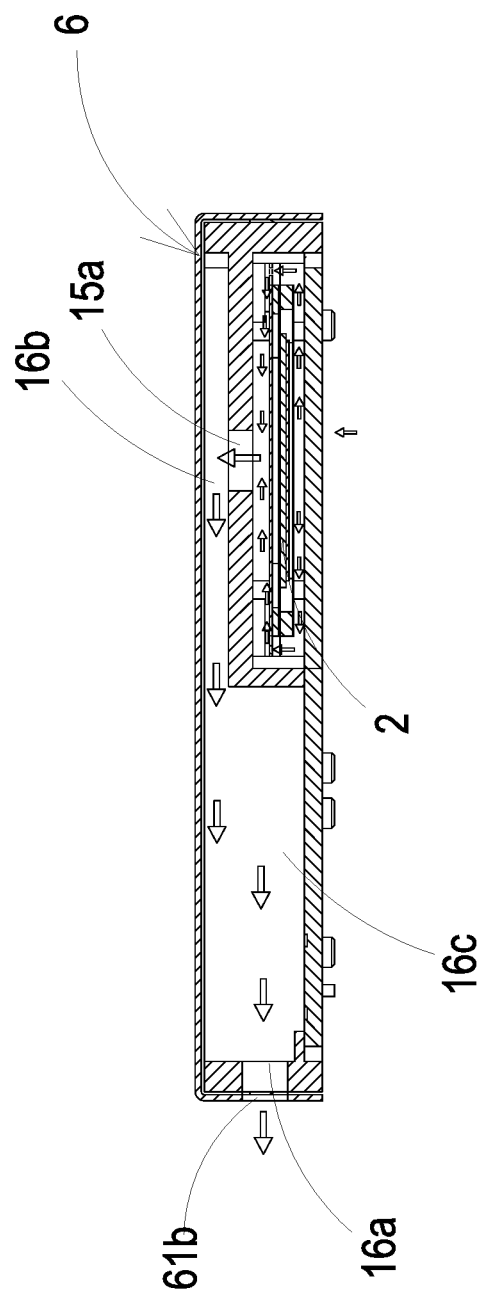

Please refer to FIGS. 8A to 8C. FIGS. 8A to 8C schematically illustrate gas flowing paths of the particle detecting module. Firstly, as shown in FIG. 8A, the gas is inhaled through the inlet opening 61a of the outer cover 6, flows into the gas-inlet groove 14 of the base 1 through the gas-inlet 14a, and is transported to the position of the particulate sensor 5. Further as shown in FIG. 8B, the piezoelectric actuator 2 is enabled continuously to inhale the gas in the inlet path, and it facilitates the gas to be introduced rapidly, flow stably, and be transported above the particulate sensor 5. At this time, a projecting light beam emitted from the laser component 4 passes through the transparent window 14b to irritate the suspended particles contained in the gas flowing above the particulate sensor 5 in the gas-inlet groove 14. When the suspended particles contained in the gas are irradiated to generate scattered light spots, the scattered light spots are received and calculated by the particulate sensor 5 for obtaining related information about the sizes and the concentration of the suspended particles contained in the gas. Moreover, the gas above the particle sensor 5 is continuously driven and transported by the piezoelectric actuator 2, flows into the ventilation hole 15a of the gas-guiding-component loading region 15, and is transported to the first section 16b of the gas-outlet groove 16. As shown in FIG. 8C, after the gas flows into the first section 16b of the gas-outlet groove 16, the gas is continuously transported into the first section 16b by the piezoelectric actuator 2, the gas in the first section 16b is pushed to the second section 16c. Finally, the gas is discharged out through the gas-outlet 16a and the outlet opening 61b.

Figure 9:
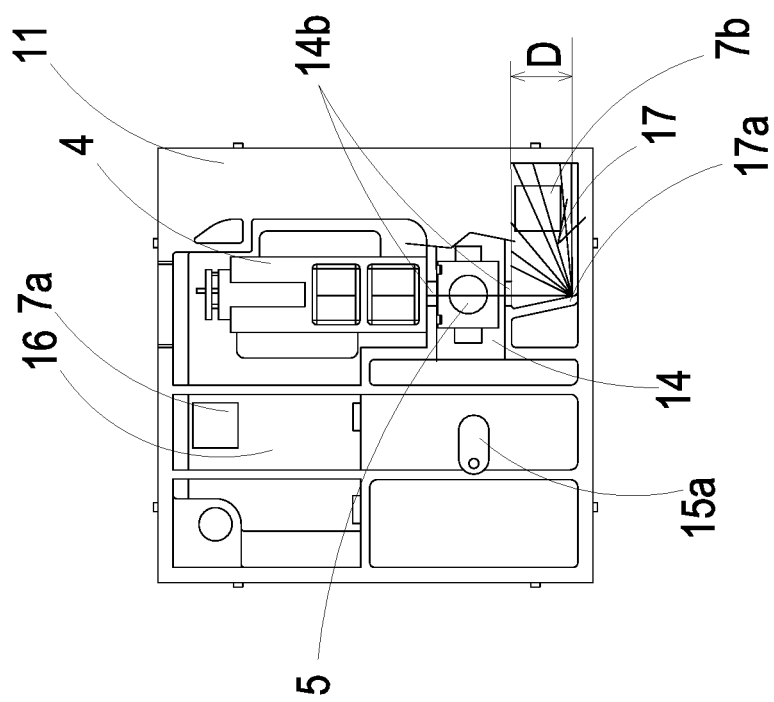
FIG. 9 schematically illustrates a light beam path emitted from the laser component.

As shown in FIG. 9, the base 1 further includes a light trapping region 17. The light trapping region 17 is hollowed out from the first surface 11 to the second surface 12 and spatially corresponds to the laser loading region 13. In the embodiment, the light trapping region 17 is corresponding to the transparent window 14b so that the light beam emitted by the laser component 4 is projected into the light trapping region 17. The light trapping region 17 includes a light trapping structure 17a having an oblique cone surface. The light trapping structure 17a spatially corresponds to the light beam path emitted from the laser component 4. In addition, the projecting light beam emitted from the laser component 4 is reflected into the light trapping region 17 through the oblique cone surface of the light trapping structure 17a. It prevents the projecting light beam from being reflected to the position of the particulate sensor 5. In the embodiment, a light trapping distance D is maintained between the transparent window 14b and a position where the light trapping structure 17a receives the projecting light beam. Preferably but not exclusively, the light trapping distance is greater than 3 mm. When the light trapping distance D is less than 3 mm, the projecting light beam projected on the light trapping structure 17a is easy to be reflected back to the position of the particulate sensor 5 directly due to excessive stray light generated after reflection, and it results in distortion of detection accuracy.

Please refer to FIG. 9 and FIG. 2C. The particle detecting module 100 of the present disclosure is not only utilized to detect the suspended particles in the gas, but also further utilized to detect the characteristics of the introduced gas. In the embodiment, the particle detecting module 100 further includes a first volatile-organic-compound sensor 7a. The first volatile-organic-compound sensor 7a is positioned and disposed on the driving circuit board 3, electrically connected to the driving circuit board 3, and accommodated in the gas-outlet groove 16, so as to detect the gas flowing through the outlet path of the gas-outlet groove 16. Thus, the concentration of volatile organic compounds contained in the gas in the outlet path is detected. In the embodiment, the particle detecting module 100 further includes a second volatile-organic-compound sensor 7b. The second volatile-organic-compound sensor 7b is positioned and disposed on the driving circuit board 3, and electrically connected to the driving circuit board 3. In the embodiment, the second volatile-organic-compound sensor 7b is accommodated in the light trapping region 17. Thus, the concentration of volatile organic compounds contained in the gas flowing through the inlet path of the gas-inlet groove 14 and transported into the light trapping region 17 through the transparent window 14b is detected.

Figure 12:
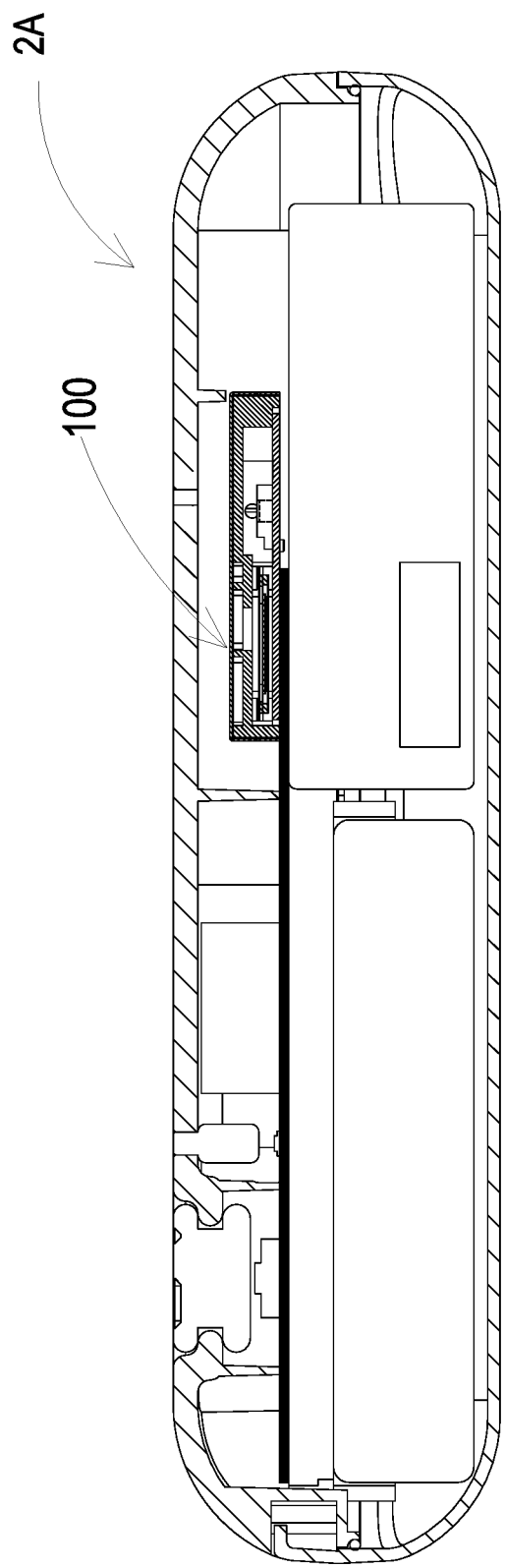
FIG. 12 is a schematic cross-sectional view illustrating the particle detecting module applied to a miniaturized portable electronic device.
Figure 13:
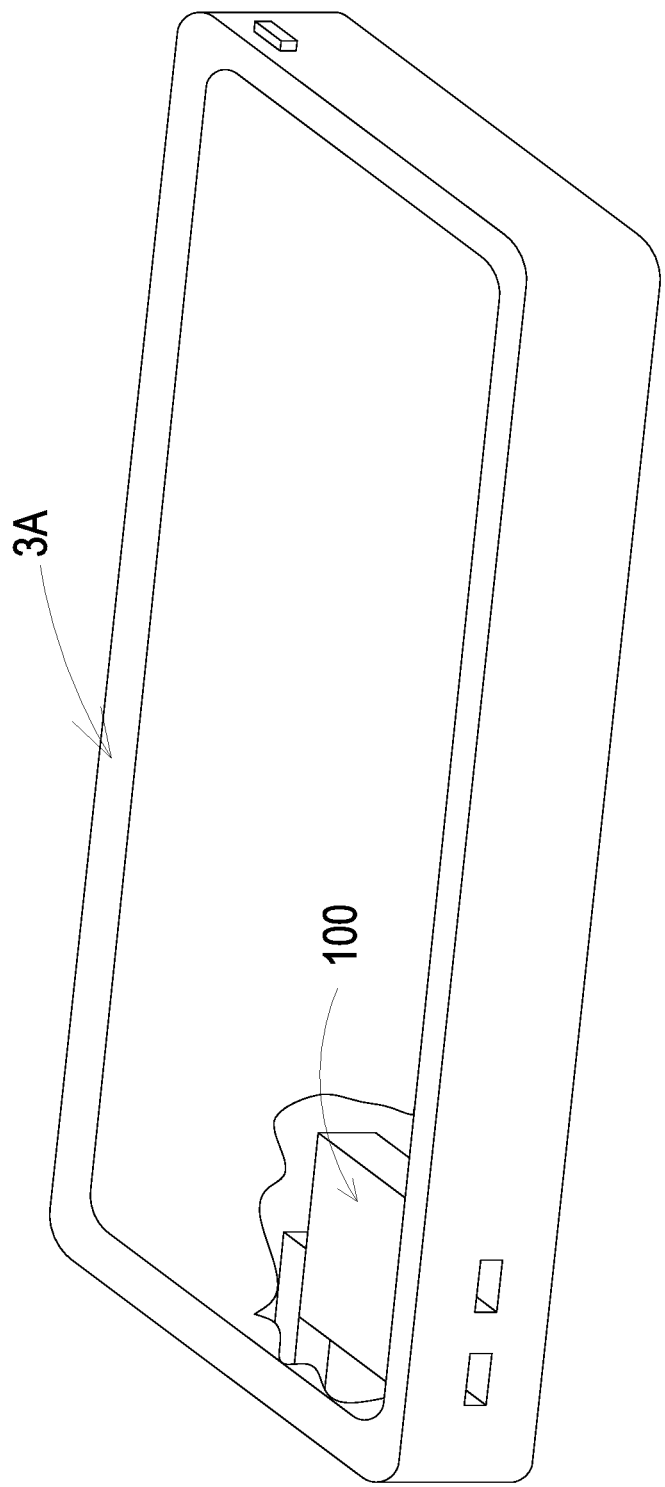
FIG. 13 is a schematic perspective view illustrating the particle detecting module embedded in a miniaturized mobile device.

As described above, the particle detecting module 100 of the present disclosure is designed to have a proper configuration of the laser loading region 13, the gas-inlet groove 14, the gas-guiding-component loading region 15 and the gas-outlet groove 16 on the base 1. The base 1 is further matched with the outer cover 6 and the driving circuit board 3 to achieve the sealing design. In that, the first surface 11 of the base 1 is covered with the outer cover 6, and the second surface 12 of the base 1 is covered with the driving circuit board 3, so that the inlet path is collaboratively defined by the gas-inlet groove 14 and the driving circuit board 3, and the outlet path is collaboratively defined by the gas-outlet groove 16, the outer cover 6 and the driving circuit board 3. The gas flowing path is formed in one layer. It facilitates the particle detecting module 100 to reduce the thickness of the overall structure. In that, the particle detecting module 100 has the length L ranging from 10 mm to 35 mm, the width W ranging from 10 mm to 35 mm, and the thickness H ranging from 1 mm to 6.5 mm. It facilitates the particle detecting module 100 to achieve the combination of a miniaturized portable electronic device 2A shown in FIG. 12, or achieve the combination of a miniaturized mobile device 3A shown in FIG. 13. It is easy for users to carry to detect the concentration of suspended particles in the surrounding environment.

Figure 10A:
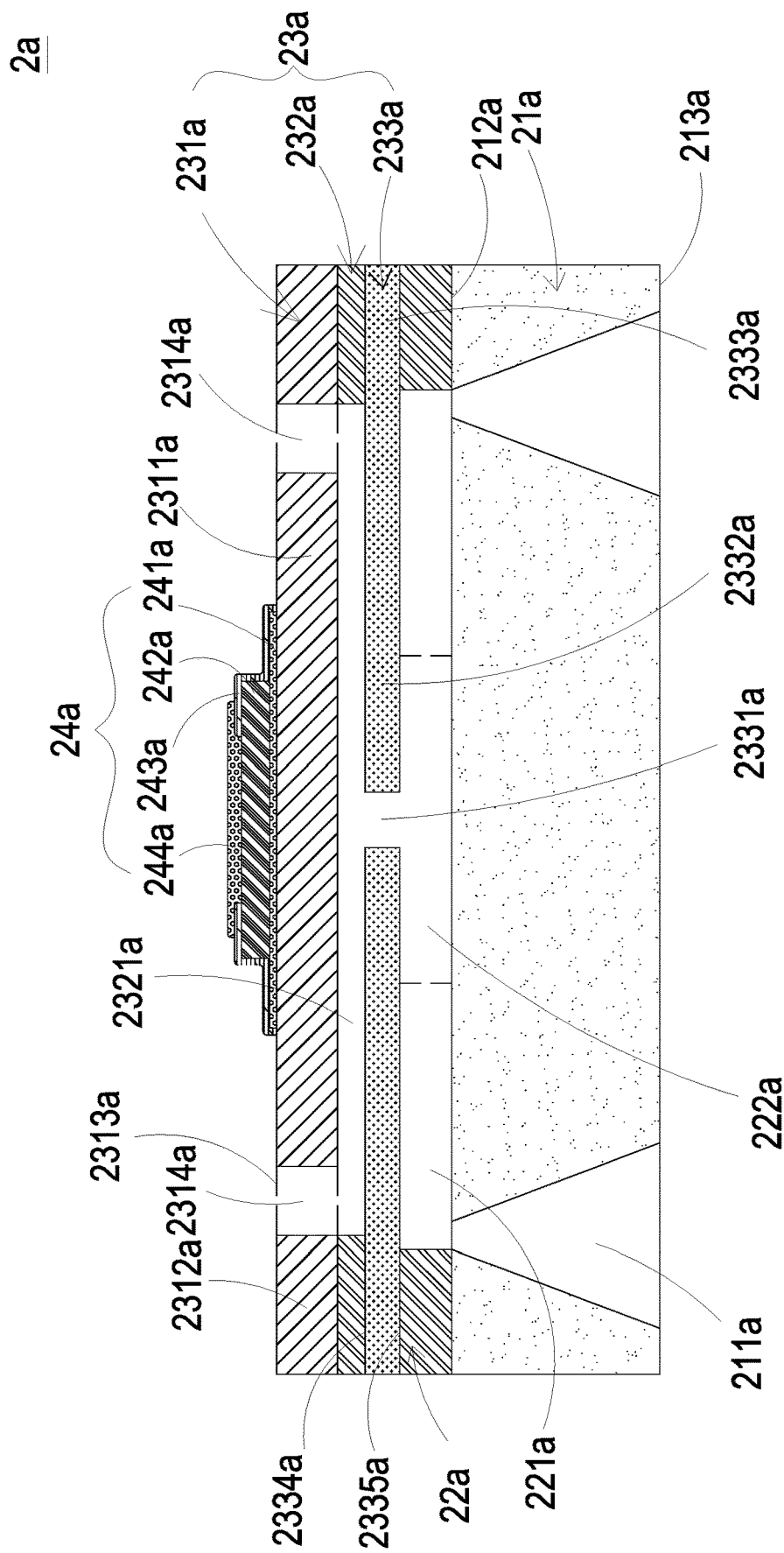
FIG. 10A is a schematic cross-sectional view illustrating a MEMS pump.
Figure 10B:
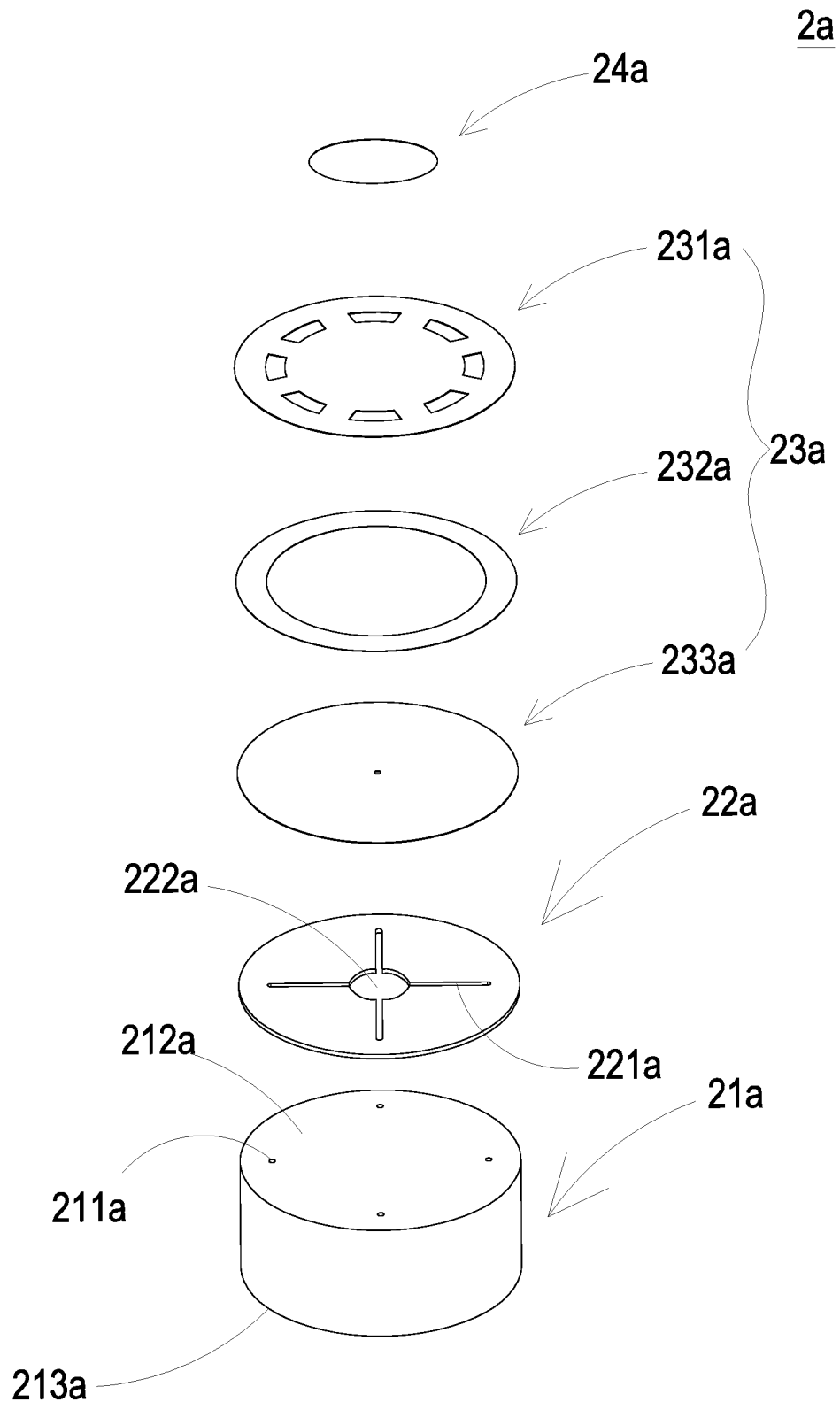
FIG. 10B is a schematic exploded view illustrating the MEMS pump.

In addition, the piezoelectric actuator 2 in the above embodiment is replaced with a MEMS pump 2a in another embodiment. Please refer to FIG. 10A and FIG. 10B. The MEMS pump 2a includes a first substrate 21a, a first oxidation layer 22a, a second substrate 23a and a piezoelectric component 24a.

Preferably but not exclusively, the first substrate 21a is a Si wafer and has a thickness ranging from 150 μm to 400 μm. The first substrate 21a includes a plurality of inlet apertures 211a, a first surface 212a and a second surface 213a. In the embodiment, there are four inlet apertures 211a, but the present disclosure is not limited thereto. Each inlet aperture 211a penetrates from the second surface 213a to the first surface 212a. In order to improve the inlet-inflow effect, the plurality of inlet apertures 211a are tapered-shaped, and the size is decreased from the second surface 213a to the first surface 212a.

The first oxidation layer 22a is a silicon dioxide ($SiO_2$) thin film and has the thickness ranging from 10 μm to 20 μm. The first oxidation layer 22a is stacked on the first surface 212a of the first substrate 21a. The first oxidation layer 22a includes a plurality of convergence channels 221a and a convergence chamber 222a. The numbers and the arrangements of the convergence channels 221a and the inlet apertures 211a of the first substrate 21a are corresponding to each other. In the embodiment, there are four convergence channels 221a. First ends of the four convergence channels 221a are in fluid communication with the four inlet apertures 211a of the first substrate 21a, and second ends of the four convergence channels 221a are in fluid communication with the convergence chamber 222a. Thus, after the gas is inhaled through the inlet apertures 211a, the gas flows through the corresponding convergence channels 221a and is converged into the convergence chamber 222a.

Preferably but not exclusively, the second substrate 23a is a silicon on insulator (SOI) wafer, and includes a silicon wafer layer 231a, a second oxidization layer 232a and a silicon material layer 233a. The silicon wafer layer 231a has a thickness ranging from 10 μm to 20 μm, and includes an actuating portion 2311a, an outer peripheral portion 2312a, a plurality of connecting portions 2313a and a plurality of fluid channels 2314a. The actuating portion 2311a is in a circular shape. The outer peripheral portion 2312a is in a hollow ring shape and disposed around the actuating portion 2311a. The plurality of connecting portions 2313a are connected between the actuating portion 2311a and the outer peripheral portion 2312a, respectively, so as to connect the actuating portion 2311a and the outer peripheral portion 2312a for elastically supporting. The plurality of fluid channels 2314a are disposed around the actuating portion 2311a and located between the connecting portions 2313a.

The second oxidation layer 232a is a silicon monoxide (SiO) layer and has a thickness ranging from 0.5 μm to 2 μm. The second oxidation layer 232a is formed on the silicon wafer layer 231a and in a hollow ring shape. A vibration chamber 2321a is collaboratively defined by the second oxidation layer 232a and the silicon wafer layer 231a. The silicon material layer 233a is in a circular shape, disposed on the second oxidation layer 232a and bonded to the first oxide layer 22a. The silicon material layer 233a is a silicon dioxide ($SiO_2$) thin film and has a thickness ranging from 2 μm to 5 μm. In the embodiment, the silicon material layer 223a includes a through hole 2331a, a vibration portion 2332a, a fixing portion 2333a, a third surface 2334a and a fourth surface 2335a. The through hole 2331a is formed at a center of the silicon material layer 233a. The vibration portion 2332a is disposed around the through hole 2331a and vertically corresponds to the vibration chamber 2321a. The fixing portion 2333a is disposed around the vibration portion 2332a and located at a peripheral region of the silicon material layer 233a. The silicon material layer 233a is fixed on the second oxidation layer 232a through the fixing portion 2333a. The third surface 2334a is connected to the second oxidation layer 232a. The fourth surface 2335a is connected to the first oxidation layer 22a. The piezoelectric component 24a is stacked on the actuating portion 2311a of the silicon wafer layer 231a.

The piezoelectric component 24a includes a lower electrode layer 241a, a piezoelectric layer 242a, an insulation layer 243a and an upper electrode layer 244a. The lower electrode 241a is stacked on the actuating portion 2311a of the silicon wafer layer 231a. The piezoelectric layer 242a is stacked on the lower electrode layer 241a. The piezoelectric layer 242a and the lower electrode layer 241a are electrically connected through the contact area thereof. In addition, the width of the piezoelectric layer 242a is less than the width of the lower electrode layer 241a, so that the lower electrode layer 241a is not completely covered by the piezoelectric layer 242a. The insulation layer 243a is stacked on a partial surface of the piezoelectric layer 242a and a partial surface of the lower electrode layer 241a, which is uncovered by the piezoelectric layer 242a. The upper electrode layer 244a is stacked on the insulation layer 243a and a remaining surface of the piezoelectric layer 242a without the insulation layer 243a disposed thereon, so that the upper electrode layer 244a is contacted and electrically connected with the piezoelectric layer 242a. At the same time, the insulation layer 243a is used for insulation between the upper electrode layer 244a and the lower electrode layer 241a, so as to avoid the short circuit caused by direct contact between the upper electrode layer 244a and the lower electrode layer 241a.

Figure 11A:
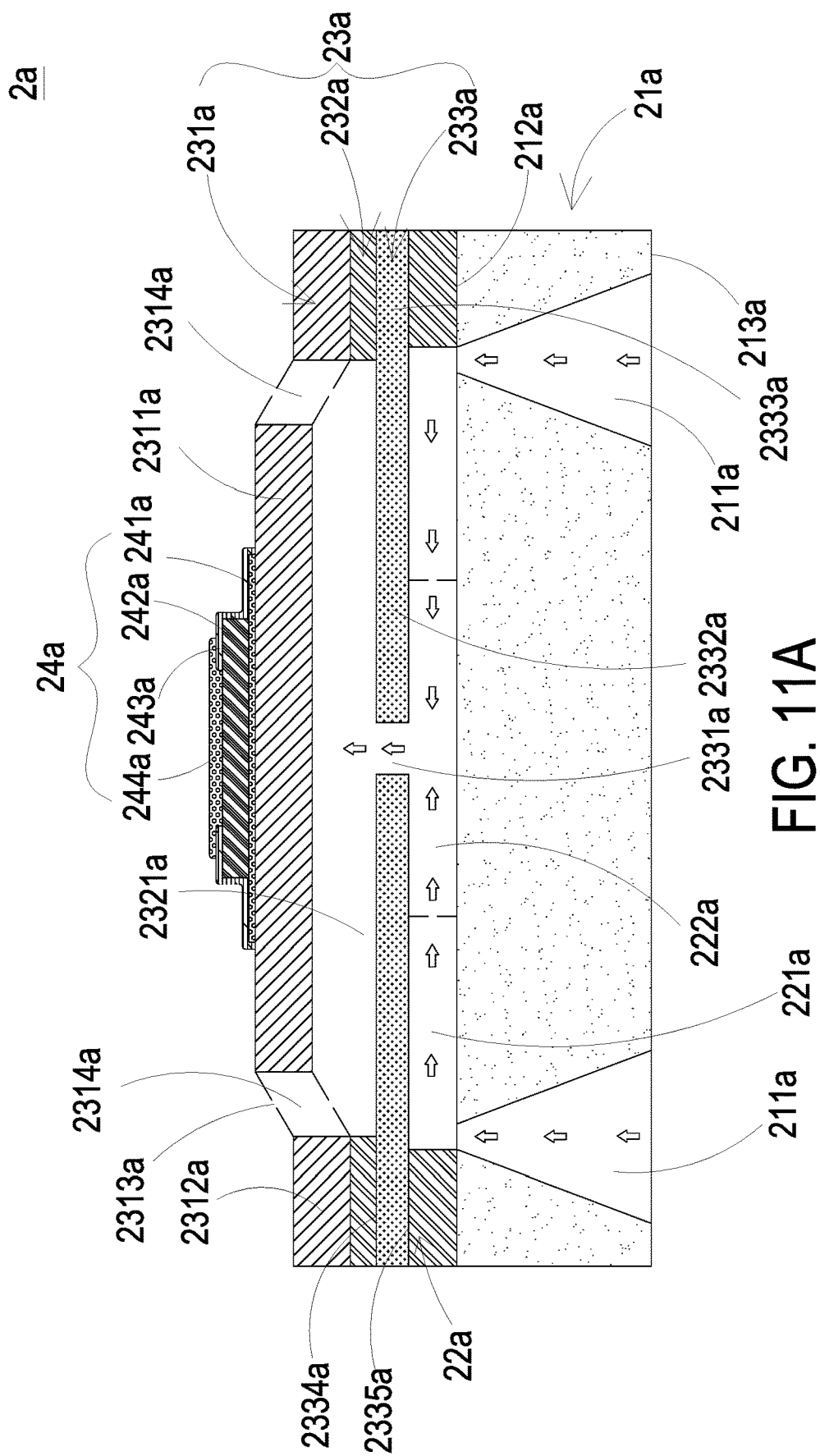
FIGS. 11A to 11C schematically illustrate the actions of the MEMS pump.
Figure 11B:
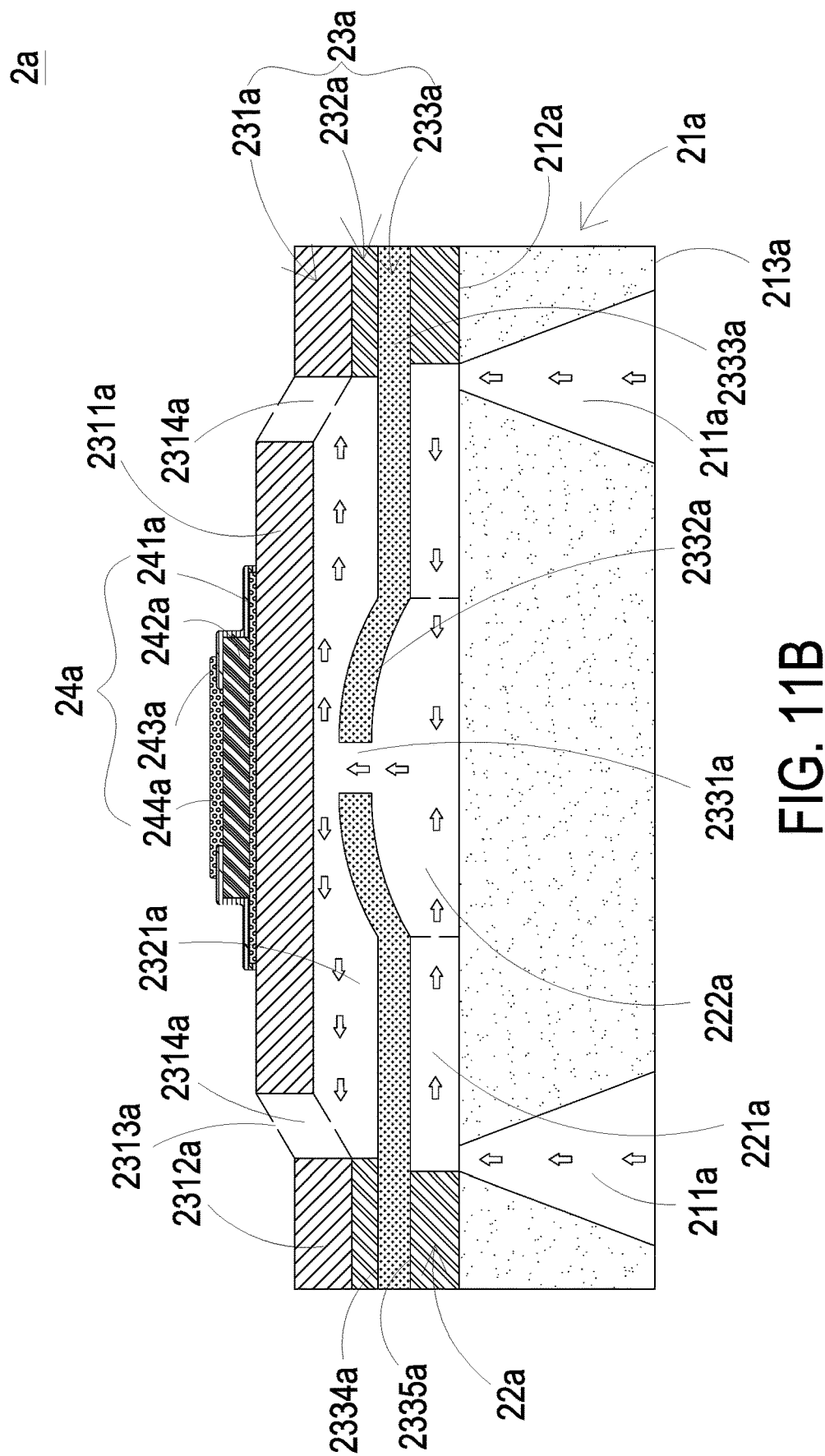
Figure 11C:
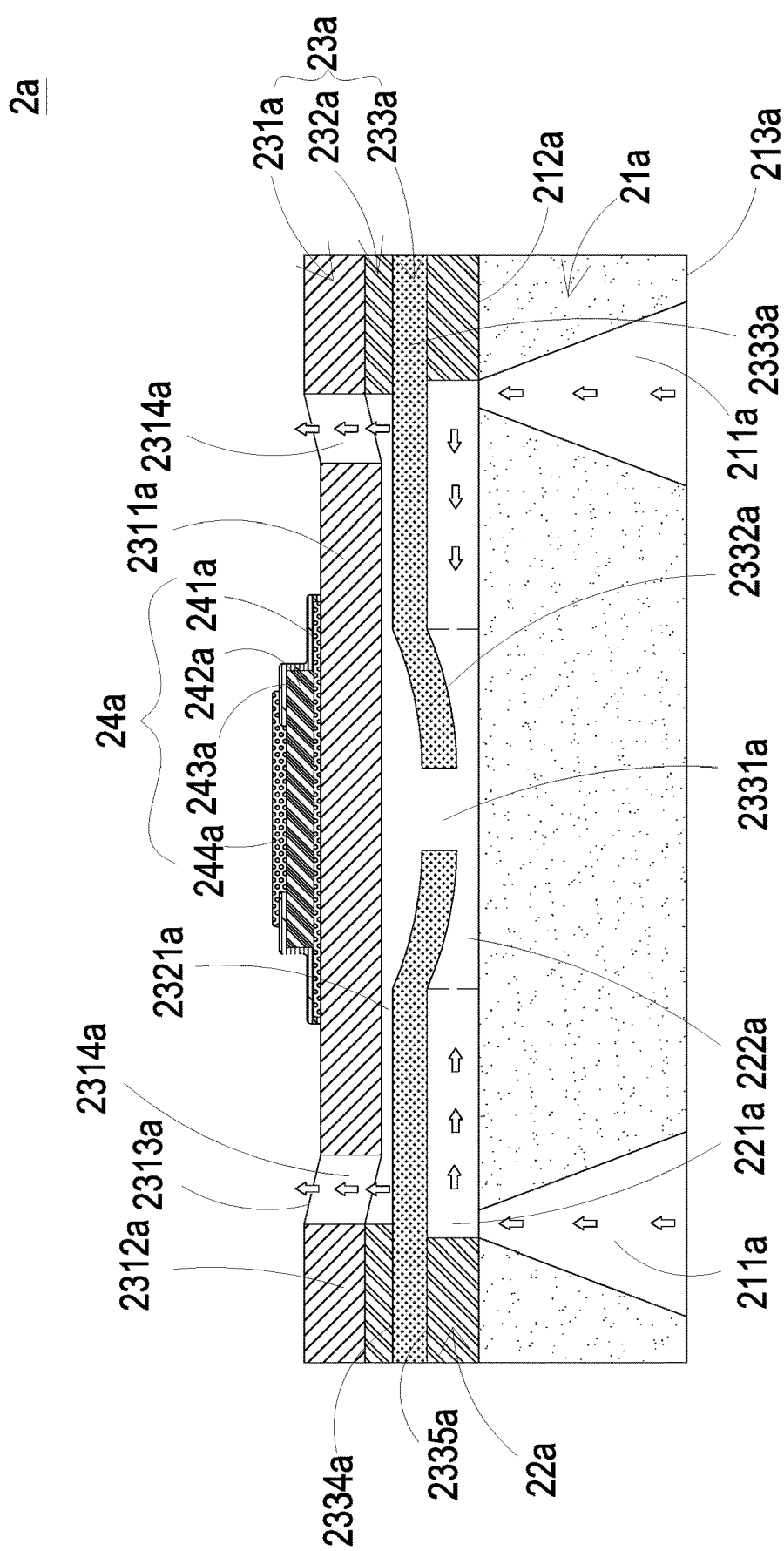

Please refer to FIGS. 11A to 11C. FIGS. 11A to 11C schematically illustrate the actions of the MEMS pump. As shown in FIG. 11A, a driving voltage and a driving signal (not shown) transmitted from the driving circuit board 3 are received by the lower electrode layer 241a and the upper electrode layer 244a of the piezoelectric component 24a, and further transmitted to the piezoelectric layer 242a. After the piezoelectric layer 242a receives the driving voltage and the driving signal, the deformation of the piezoelectric layer 242a is generated due to the influence of the reverse piezoelectric effect. In that, the actuating portion 2311a of the silicon wafer layer 231a is driven to displace. When the piezoelectric component 24a drives the actuating portion 2311a to move upwardly, the actuating portion 2311a is separated away from the second oxidation layer 232a to increase the distance therebetween. In that, the volume of the vibration chamber 2321a of the second oxidation layer 232a is expended rapidly, the internal pressure of the vibration chamber 2321a is decreased to form a negative pressure, and the gas in the convergence chamber 222a of the first oxidation layer 22a is inhaled into the vibration chamber 2321a through the through hole 2331a. Further as shown in FIG. 11B, when the actuating portion 2311a is driven by the piezoelectric component 24a to move upwardly, the vibration portion 2332a of the silicon material layer 233a is moved upwardly due to the influence of the resonance principle. When the vibration portion 2332a is displaced upwardly, the space of the vibration chamber 2321a is compressed and the gas in the vibration chamber 2321a is pushed to move to the fluid channels 2314a of the silicon wafer layer 231a. In that, the gas flows upwardly through the fluid channel 2314a and is discharged out. Moreover, when the vibration portion 2332a is displaced upwardly to compress the vibration chamber 2321a, the volume of the convergence chamber 222a is expended due to the displacement of the vibration portion 2332a, the internal pressure of the convergence chamber 222a is decreased to form a negative pressure, and the gas outside the MEMS pump 2a is inhaled into the convergence chamber 222a through the inlet apertures 211a. As shown in FIG. 11C, when the piezoelectric component 24a is enabled to drive the actuating portion 2311a of the silicon wafer layer 231a to displace downwardly, the gas in the vibration chamber 2321a is pushed to flow to the fluid channels 2314a, and is discharged out. At the same time, the vibration portion 2332a of the silicon material layer 233a is driven by the actuating portion 2311a to displace downwardly, and the gas in the convergence chamber 222a is compressed to flow to the vibration chamber 2321a. Thereafter, when the piezoelectric component 24a drives the actuating portion 2311a to displace upwardly, the volume of the vibration chamber 2321a is greatly increased, and then there is a higher suction force to inhale the gas into the vibration chamber 2321a. By repeating the above actions, the actuating portion 2311a is continuously driven by the piezoelectric element 24a to displace upwardly and downwardly, and further to drive the vibration portion 2332a to displace upwardly and downwardly. By changing the internal pressure of the MEMS pump 2a, the gas is inhaled and discharged continuously, thereby achieving the actions of the MEMS pump 2a.

Certainly, in order to embed the particle detecting module 100 of the present disclosure in the mobile device 3A, the piezoelectric actuator 2 of the present disclosure can be replaced by the structure of the MEMS pump 2a, so that entire size of the particle detecting module 100 of the present disclosure is further reduced. Preferably but not exclusively, the particle detecting module 100 has the length ranging from 2 mm to 4 mm, the width ranging from 2 mm to 4 mm, and the thickness ranging from 1 mm to 3.5 mm. It facilitates the particle detecting module 100 to be implemented in the mobile device, for example the current smart phone with a thickness of 5 mm. With the particle detecting module 100 embedded in the smart phone directly, the user can immediately detect the air quality in the surrounding environment.

From the above descriptions, the present disclosure provides a particle detecting module. The laser component is disposed on the driving circuit board directly, the driving circuit board is attached to the second surface of the base, and the first surface of the base is attached by the outer cover, so that an inlet path is collaboratively defined by the gas-inlet groove and the driving circuit board, and an outlet path is defined by the gas-outlet groove. It benefits to reduce the thickness of the particle detecting module greatly. In addition, the piezoelectric actuator and the laser component are separated, and supplemented with the design of the gas flowing path. It prevents the actions of the piezoelectric actuator from interfering the operations of the laser component and the particulate sensor. Moreover, it is beneficial of reducing the volume of the particle detecting module. Its length can be reduced and ranging from 10 mm to 35 mm. Its width can be reduced and ranging from 10 mm to 35 mm. Its thickness can be reduced and ranging from 1 mm to 6.5 mm. Thus, the particle detecting module of the present disclosure is easy to carry. Furthermore, with the light trapping structure in the light trapping region, when the light beam emitted from the laser component passes through the particulate sensor and contacts with the base to generate the scattered light, it benefits to reduce the probability of the scattered light entering the particle sensor again. It is helpful of improving the detection efficiency of the particulate sensor. The present disclosure includes the industrial applicability and the inventive steps.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:
1. A particle detecting module, comprising:
 a base comprising:
  a first surface;
  a second surface opposite to the first surface;
  a laser loading region hollowed out from the first surface to the second surface;
  a gas-inlet groove concavely formed from the second surface and disposed adjacent to the laser loading region, wherein the gas-inlet groove comprises a gas-inlet and two lateral walls, the gas-inlet is in communication with an environment outside the base, and a transparent window is opened on the lateral wall and is in communication to the laser loading region;

a gas-guiding-component loading region concavely formed from the second surface and in communication with the gas-inlet groove, wherein a ventilation hole penetrates a bottom surface of the gas-guiding-component loading region; and a gas-outlet groove concavely formed from the first surface, spatially corresponding to the bottom surface of the gas-guiding-component loading region, and hollowed out from the first surface to the second surface in a region where the first surface is not aligned with the gas-guiding-component loading region, wherein the gas-outlet groove is in communication with the ventilation hole, and a gas-outlet is disposed in the gas-outlet groove and in communication with the environment outside the base;

a piezoelectric actuator accommodated in the gas-guiding-component loading region;

a driving circuit board covering and attached to the second surface of the base;

a laser component positioned and disposed on the driving circuit board, electrically connected to the driving circuit board, and accommodated in the laser loading region, wherein a light beam path emitted from the laser component passes through the transparent window and extends in a direction perpendicular to the gas-inlet groove, thereby forming an orthogonal direction with the gas-inlet groove;

a particulate sensor positioned and disposed on the driving circuit board, electrically connected to the driving circuit board, and disposed at an orthogonal position where the gas-inlet groove intersects the light beam path of the laser component in the orthogonal direction, so that suspended particles passing through the gas-inlet groove and irradiated by a projecting light beam emitted from the laser component are detected; and an outer cover covering the first surface of the base and comprising a side plate, wherein the side plate has an inlet opening spatially corresponding to the gas-inlet and an outlet opening spatially corresponding to the gas-outlet, respectively, wherein the base, the piezoelectric actuator, the driving circuit board, the laser component, the particulate sensor and the outer cover are produced by tiny materials to form a modular structure, and the modular structure has a length, a width and a thickness, wherein the first surface of the base is covered with the outer cover, and the second surface of the base is covered with the driving circuit board, so that an inlet path is defined by the gas-inlet groove, and an outlet path is defined by the gas-outlet groove, wherein the gas is inhaled from the environment outside the base by the piezoelectric actuator, transported into the inlet path through the inlet opening, and passes through the particulate sensor to detect a concentration of the suspended particles contained in the gas, and the gas transported through the piezoelectric actuator is transported out of the outlet path through the ventilation hole and then discharged through the outlet opening.

2. The particle detecting module according to claim 1, wherein the length of the modular structure is ranging from 1 μm to 999 μm, the width of the modular structure is ranging from 1 μm to 999 μm, and the thickness of the modular structure is ranging from 1 μm to 999 μm.

3. The particle detecting module according to claim 1, wherein the length of the modular structure is ranging from 1 nm to 999 nm, the width of the modular structure is ranging from 1 nm to 999 nm, and the thickness of the modular structure is ranging from 1 nm to 999 nm.

4. The particle detecting module according to claim 1, wherein four positioning notches are disposed at four corners of the gas-guiding-component loading region, respectively, and the piezoelectric actuator is disposed and positioned in the gas-guiding-component loading region.

5. The particle detecting module according to claim 1, wherein the base comprises a light trapping region hollowed out from the first surface to the second surface and spatially corresponding to the laser loading region, wherein the light trapping region comprises a light trapping structure having an oblique cone surface and spatially corresponding to the light beam path.

6. The particle detecting module according to claim 5, wherein a light trapping distance is maintained between the transparent window and a position where the light trapping structure receives the projecting light beam.

7. The particle detecting module according to claim 5, wherein the light trapping distance is greater than 3 mm.

8. The particle detecting module according to claim 1, wherein the particulate sensor is a PM2.5 sensor.

9. The particle detecting module according to claim 1, wherein the piezoelectric actuator comprises:

a gas-injection plate comprising a plurality of connecting members, a suspension plate and a hollow aperture, wherein the suspension plate is permitted to undergo a bending deformation, and the hollow aperture is formed at a center of the suspension plate, wherein the suspension plate is fastened through and elastically supported by the plurality of connecting elements, a flowing chamber is formed between the gas-injection plate and the bottom surface of the gas-guiding-component loading region, and at least one vacant is formed between the plurality of connecting elements and the suspension plate;

a chamber frame carried and stacked on the suspension plate;

an actuator element carried and stacked on the chamber frame for being driven in response to an applied voltage to undergo the bending deformation in a reciprocating manner;

an insulation frame carried and stacked on the actuator element; and a conductive frame carried and stacked on the insulation frame, wherein a resonance chamber is formed among the actuator element, the chamber frame and the suspension plate, wherein when the actuator element is enabled to drive the gas-injection plate to move in resonance, the suspension plate of the gas-injection plate is driven to generate the bending deformation in the reciprocating manner, the gas flows through the vacant space, enters the flowing chamber, and is discharged out, so as to achieve gas transportation.

10. The particle detecting module according to claim 8, wherein the actuator element comprises:

a piezoelectric carrying plate carried and stacked on the chamber frame;

an adjusting resonance plate carried and stacked on the piezoelectric carrying plate; and a piezoelectric plate carried and stacked on the adjusting resonance plate, wherein the piezoelectric plate is configured to drive the piezoelectric carrying plate and the adjusting resonance plate to generate the bending deformation in the reciprocating manner by the applied voltage.

11. The particle detecting module according to claim 1, further comprising a first volatile-organic-compound sensor positioned and disposed on the driving circuit board, electrically connected to the driving circuit board, and accommodated in the gas-outlet groove, so as to detect the gas flowing through the outlet path of the gas-outlet groove.

12. The particle detecting module according to claim 5, further comprising a second volatile-organic-compound sensor positioned and disposed on the driving circuit board, electrically connected to the driving circuit board, and accommodated in the light trapping region, so as to detect the gas flowing through the inlet path of the gas-inlet groove and transported into the light trapping region through the transparent window.

13. The particle detecting module according to claim 1, wherein the particle detecting module has a length ranging from 10 mm to 35 mm, a width ranging from 10 to 35 mm, and a thickness ranging from 1 mm to 6.5 mm.

14. The particle detecting module according to claim 1, wherein the piezoelectric actuator is a microelectromechanical systems (MEMS) pump comprising:
  a first substrate having a plurality of inlet apertures, wherein the plurality of inlet apertures are tapered-shaped;
  a first oxidation layer stacked on the first substrate, wherein the first oxidation layer comprises a plurality of convergence channels and a convergence chamber, and the plurality of convergence channels are in fluid communication between the convergence chamber and the plurality of inlet apertures;
  a second substrate combined with the first substrate and comprising:
    a silicon wafer layer, comprising:
      an actuating portion being in a circular shape;
      an outer peripheral portion being in a hollow ring shape and disposed around the actuating portion;
      a plurality of connecting portions connected between the actuating portion and the outer peripheral portion, respectively; and
      a plurality of fluid channels disposed around the actuating portion and located between the connecting portions;
    a second oxidation layer formed on the silicon wafer layer and being in a hollow ring shape, wherein a vibration chamber is collaboratively defined by the second oxidation layer and the silicon wafer layer; and
    a silicon material layer being in a circular shape, disposed on the second oxidation layer and bonded to the first oxide layer, comprising:
      a through hole formed at a center of the silicon material layer;
      a vibration portion disposed around the through hole; and
      a fixing portion disposed around the vibration portion; and
  a piezoelectric component being in a circular shape and stacked on the actuating portion of the silicon wafer layer.

15. The particle detecting module according to claim 14, wherein the piezoelectric component comprises:
  a lower electrode layer;
  a piezoelectric layer stacked on the lower electrode layer;
  an insulation layer stacked on a partial surface of piezoelectric layer and a partial surface of the lower electrode layer; and
  an upper electrode layer stacked on the insulation layer and a remaining surface of the piezoelectric layer without the insulation layer disposed thereon, so as to electrically connect with piezoelectric layer.

* * * * *